(12) United States Patent
Suzuki et al.

(10) Patent No.: US 8,467,065 B2
(45) Date of Patent: Jun. 18, 2013

(54) REFLECTIVE OPTICAL SENSOR AND IMAGE FORMING APPARATUS

(75) Inventors: Hidemasa Suzuki, Kanagawa (JP); Koji Masuda, Kanagawa (JP); Takeshi Ueda, Tokyo (JP)

(73) Assignee: Ricoh Company, Limited, Tokyo (JP)

( * ) Notice: Subject to any disclaimer, the term of this patent is extended or adjusted under 35 U.S.C. 154(b) by 338 days.

(21) Appl. No.: 12/861,494

(22) Filed: Aug. 23, 2010

(65) Prior Publication Data

US 2011/0043810 A1    Feb. 24, 2011

(30) Foreign Application Priority Data

Aug. 24, 2009  (JP) ................. 2009-192865

(51) Int. Cl.
*G01N 21/55*  (2006.01)
(52) U.S. Cl.
CPC .................... *G01N 21/55* (2013.01)
USPC ........................................................ 356/445
(58) Field of Classification Search
CPC .................................................. G01N 21/55
USPC .................................................. 356/445–448
See application file for complete search history.

(56) References Cited

U.S. PATENT DOCUMENTS

| 5,606,181 | A  | 2/1997  | Sakuma et al.  |
|-----------|----|---------|----------------|
| 6,456,314 | B1 | 9/2002  | Masuda         |
| 6,462,879 | B2 | 10/2002 | Masuda         |
| 6,496,214 | B1 | 12/2002 | Masuda et al.  |
| 6,686,946 | B2 | 2/2004  | Masuda et al.  |
| 6,697,181 | B2 | 2/2004  | Masuda         |
| 6,717,606 | B2 | 4/2004  | Masuda         |
| 6,724,414 | B2 | 4/2004  | Masuda et al.  |
| 6,771,296 | B2 | 8/2004  | Hayashi et al. |
| 6,815,663 | B2 | 11/2004 | Ueda           |
| 6,847,472 | B2 | 1/2005  | Masuda         |
| 7,068,295 | B2 | 6/2006  | Masuda         |
| 7,145,589 | B2 | 12/2006 | Amada et al.   |
| 7,253,937 | B2 | 8/2007  | Ueda et al.    |
| 7,417,777 | B2 | 8/2008  | Saisho et al.  |
| 7,450,283 | B2 | 11/2008 | Masuda         |
| 7,505,060 | B2 | 3/2009  | Amada et al.   |
| 7,570,278 | B2 | 8/2009  | Ueda           |
| 7,593,150 | B2 | 9/2009  | Masuda         |

(Continued)

FOREIGN PATENT DOCUMENTS

| JP | 64-35466 A   | 2/1989 |
|----|--------------|--------|
| JP | 2002-72612 A | 3/2002 |
| JP | 2003-84530 A | 3/2003 |

(Continued)

*Primary Examiner* — Michael P Stafira
(74) *Attorney, Agent, or Firm* — Dickstein Shapiro LLP

(57) ABSTRACT

A reflective optical sensor detects a position and/or a toner density of the toner pattern. The reflective optical sensor includes an illuminating system that has at least three light-emitting units, a light-receiving system that has at least three light-receiving units and receives light output from the illuminating system and reflected by the toner pattern, and an illuminating optical system that includes at least three illuminating condenser lenses individually corresponding to the at least three light-emitting units and that guides the light output from the illuminating system to the toner pattern. The at least three light-emitting units and the at least three light-receiving units are both arranged in equal distance with respect to one direction. Optical axes of the at least three illuminating condenser lenses are off-center in parallel to an axis passing through a center of and perpendicular to the corresponding light-emitting unit.

15 Claims, 36 Drawing Sheets

U.S. PATENT DOCUMENTS

| | | |
|---|---|---|
| 7,619,795 B2 | 11/2009 | Masuda |
| 7,663,657 B2 | 2/2010 | Ichii et al. |
| 7,672,032 B2 | 3/2010 | Hayashi et al. |
| 7,705,868 B2 | 4/2010 | Masuda et al. |
| 2005/0093963 A1 | 5/2005 | Masuda |
| 2006/0038873 A1* | 2/2006 | Hirai et al. .................. 347/129 |
| 2006/0274628 A1* | 12/2006 | Tanaka et al. ................ 369/100 |
| 2007/0146473 A1 | 6/2007 | Masuda |
| 2007/0253048 A1 | 11/2007 | Sakai et al. |
| 2008/0084594 A1 | 4/2008 | Masuda |
| 2009/0015896 A1 | 1/2009 | Masuda |
| 2009/0238590 A1* | 9/2009 | Masuda ......................... 399/49 |
| 2010/0008686 A1* | 1/2010 | Masuda et al. ................. 399/51 |

FOREIGN PATENT DOCUMENTS

| | | |
|---|---|---|
| JP | 2004-21164 A | 1/2004 |
| JP | 2005-238584 A | 9/2005 |
| JP | 2008-70198 A | 3/2008 |
| JP | 4110027 B2 | 4/2008 |
| JP | 4154272 B2 | 7/2008 |
| JP | 2008-276010 A | 11/2008 |

* cited by examiner

WHEN IRRADIATION IN RECTANGULAR PATTERN p4 IS PERFORMED WITH DETECTING LIGHT S10

WHEN IRRADIATION IN RECTANGULAR PATTERN p5 IS PERFORMED WITH DETECTING LIGHT S10

REFLECTIVE OPTICAL SENSOR AND IMAGE FORMING APPARATUS

CROSS-REFERENCE TO RELATED APPLICATIONS

The present application claims priority to and incorporates by reference the entire contents of Japanese Patent Application No. 2009-192865 filed in Japan on Aug. 24, 2009.

BACKGROUND OF THE INVENTION

1. Field of the Invention

The present invention relates to reflective optical sensors and image forming apparatuses and, more particularly, to a reflective optical sensor that detects at least one of a position or a toner density of a toner pattern and an image forming apparatus including the same.

2. Description of the Related Art

As an image forming apparatus forming an image with toner, a copier, a printer, a plotter, a facsimile device, a multi-function printer (MFP), and the like are widely known. With such image forming apparatuses, in general, an electrostatic latent image is formed on a surface of a drum having photosensitivity (hereinafter, also referred to as "photosensitive drum" for convenience sake) and so-called development is performed in which the toner is adhered onto the electrostatic latent image to obtain a "toner image".

To obtain a good toner image, the amount of toner provided for the development of electrostatic latent images needs to be appropriate. There are various known development methods such as a method using "a two-component developer containing toner and carrier" and a method using a mono-component developer containing toner only. The amount of toner provided to a developing unit where an electrostatic latent image is developed is also referred to as "toner density".

When the toner density is too low, a sufficient amount of toner is not provided to the electrostatic latent image resulting in the image output from the image forming apparatus (output image) having an insufficient density. On the other hand, when the toner density is too high, the density distribution of the output image is concentrated on a "high density side", making the image hard to see. To obtain a good output image, the toner density needs to be within an appropriate range.

Consequently, techniques are widely employed to control the toner density within the appropriate range. According to the techniques: a pattern is formed for detecting the toner density; the pattern is irradiated with light (detecting light); and the toner density is detected based on the change in the amount of reflected light (for example, refer to Japanese Patent Application Laid-open No. H1-35466, Japanese Patent Application Laid-open No. 2004-21164, Japanese Patent Application Laid-open No. 2002-72612, Japanese Patent No. 415-4272, and Japanese Patent No. 4110027).

A conventional sensor for detecting the toner density is structured with one or two pieces of light-emitting units or three pieces of light-emitting units having different wavelength characteristics, and one or two pieces of light-receiving units that receive reflected light. Furthermore, the length of the toner pattern in a main direction is set to 15 to 25 millimeters such that the light spot of detecting light as a whole illuminates the toner pattern even when the position of the toner pattern is displaced with respect to the sensor.

In the image forming apparatus, the advancement in color imaging and high speed processing is making a tandem type image forming apparatus having multiple photosensitive drums (generally, four pieces) more popular.

In the tandem type image forming apparatus, an out-of-color registration occurs in the output image if the positional relationship of toner images of the respective photosensitive drums is not appropriate. Accordingly, to control the positional relationship of toner images to make it appropriate, a method is widely used, according to which: a position detecting pattern is formed; the pattern is irradiated with light (detecting light); and the position of the pattern is detected from the temporal change in the amount of reflected light (for example, refer to Japanese Patent Application Laid-open No. 2008-276010 and Japanese Patent Application Laid-open No. 2005-238584).

While the toner density detecting process and the pattern position detecting process are in progress, a normal image forming cannot be carried out. When the toner density detecting process and the pattern position detecting process using a conventional reflective optical sensor are performed, the work efficiency of the normal image forming is deteriorated because it takes time to form the respective detecting patterns.

In addition, there has been a problem that the replacement cycle of toner cartridge is shortened because the toner used for detecting patterns is so-called "non-contributing toner" that does not contribute to normal image forming.

SUMMARY OF THE INVENTION

It is an object of the present invention to at least partially solve the problems in the conventional technology.

According to one aspect of the present invention, a reflective optical sensor detects at least one of a position of a toner pattern and a toner density of the toner pattern, and the reflective optical sensor includes: an illuminating system that has at least three light-emitting units; a light-receiving system that has at least three light-receiving units and receives light output from the illuminating system and reflected by the toner pattern; and an illuminating optical system that includes at least three illuminating condenser lenses individually corresponding to the at least three light-emitting units and that guides the light output from the illuminating system to the toner pattern, wherein the at least three light-emitting units and the at least three light-receiving units are both arranged in equal distance with respect to one direction, and optical axes of the at least three illuminating condenser lenses are off-center in parallel to an axis passing through a center of and perpendicular to the corresponding light-emitting unit.

Further, according to another aspect of the present invention, an image forming apparatus includes: an image carrier; a light-scanning device that scans the image carrier in a main-scanning direction with light flux modulated in response to image information to form a latent image on the image carrier; a developing device that adheres toner to the latent image to create a toner image; a transfer device that transfers the toner image to a medium; and the reflective optical sensor as described above that detects at least one of a position and a toner density of the toner pattern on the image carrier or the medium.

Further, according to still another aspect of the present invention, a reflective optical sensor detecting at least one of a position of a toner pattern and a toner density of the toner pattern, the reflective optical sensor includes: an illuminating system that has at least three light-emitting units; a light-receiving system that has at least three light-receiving units and receives light output from the illuminating system and reflected by the toner pattern; and a light-receiving optical system that includes at least three light-receiving condenser lenses individually corresponding to the at least three light-emitting units and that condenses and guides light flux reflected by the toner pattern to the light-receiving system, wherein the at least three light-emitting units and the at least three light-receiving units are both arranged in equal distance with respect to one direction, and optical axes of the at least three light-receiving condenser lenses are off-center in parallel to an axis passing through a center of and perpendicular to the corresponding light-receiving unit.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
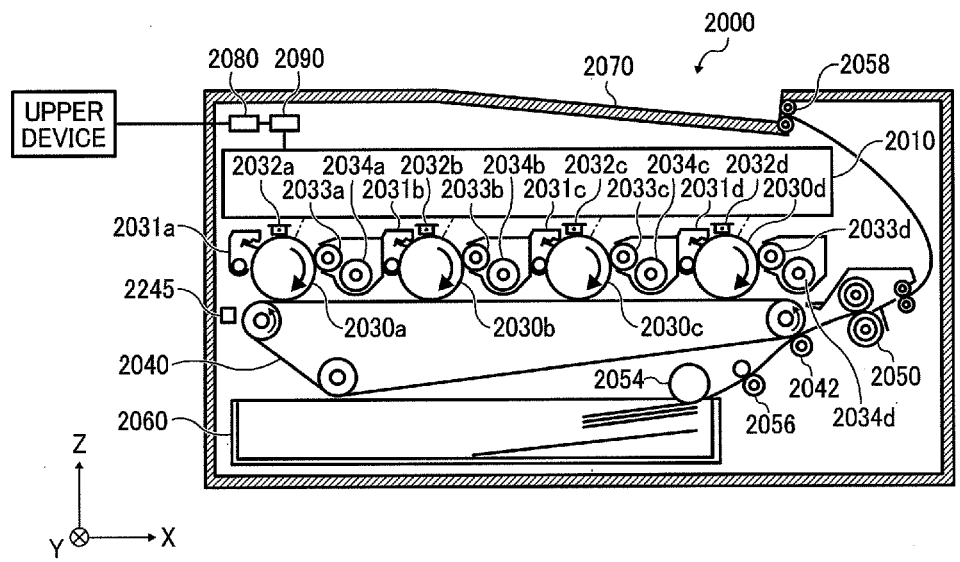
FIG. 1 is a schematic for explaining the structure of a color printer according to an embodiment of the present invention.
Figure 2:
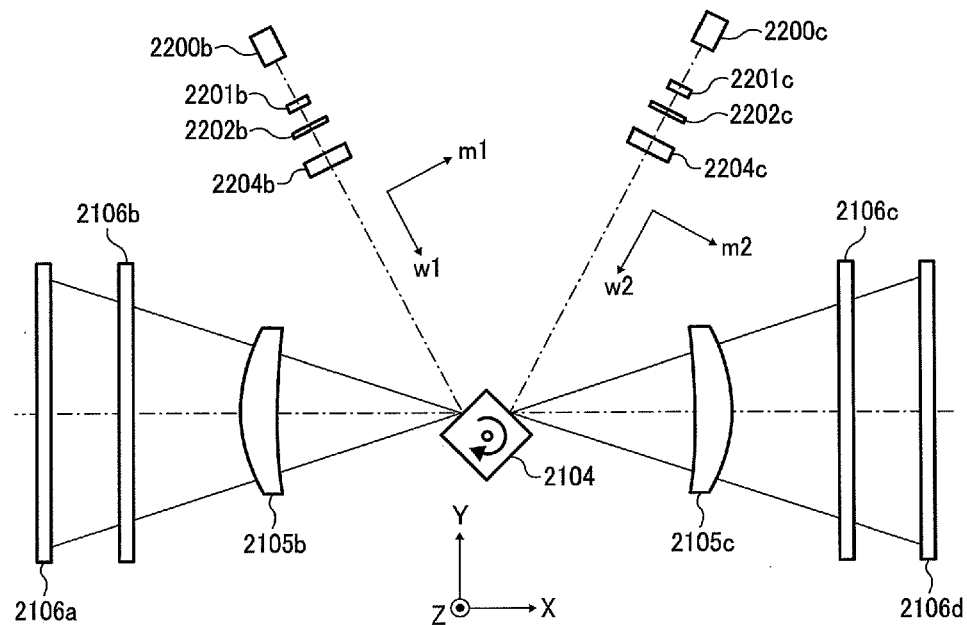
FIG. 2 is a schematic for explaining the structure of a light-scanning device (part 1)
Figure 3:
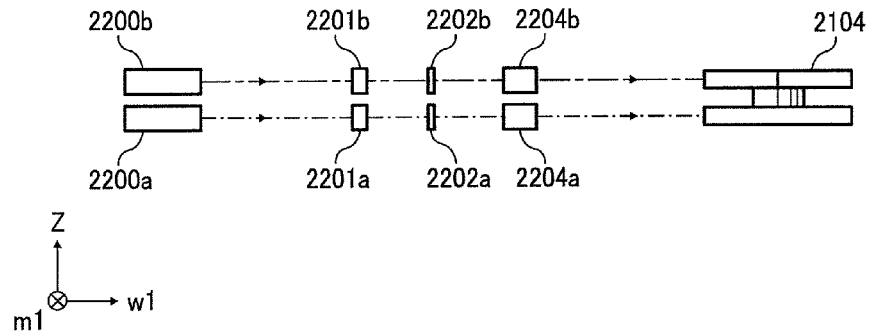
FIG. 3 is a schematic for explaining the structure of the light-scanning device (part 2)
Figure 4:
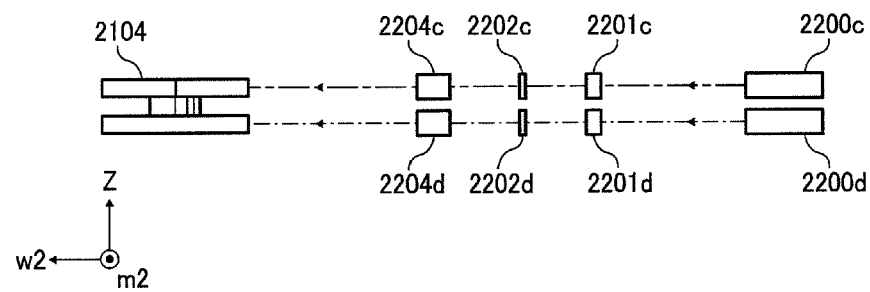
FIG. 4 is a schematic for explaining the structure of the light-scanning device (part 3)
Figure 5:
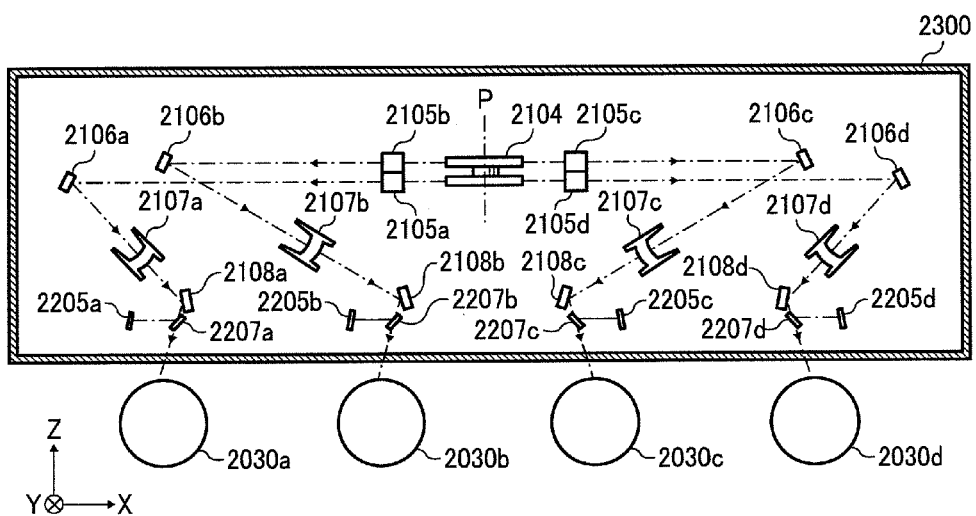
FIG. 5 is a schematic for explaining the structure of the light-scanning device (part 4)

An embodiment of the present invention will be explained based on FIGS. 1 to 45E below. FIG. 1 schematically depicts the structure of a color printer 2000 as an image forming apparatus according to the present embodiment.

The color printer 2000 is a tandem-type multi-color printer overlaying four colors (black, cyan, magenta, and yellow) to form a full color image, and includes, for example, a light-scanning device 2010, four photosensitive drums (2030a, 2030b, 2030c, and 2030d), four cleaning units (2031a, 2031b, 2031c, and 2031d), four charging devices (2032a, 2032b, 2032c, and 2032d), four developing rollers (2033a, 2033b, 2033c, and 2033d), four toner cartridges (2034a, 2034b, 2034c, and 2034d), a transfer belt 2040, a transfer roller 2042, a fuser roller 2050, a feed roller 2054, a registration roller pair 2056, a delivery roller 2058, a paper feed tray 2060, a catch tray 2070, a communication control device 2080, a toner pattern detector 2245, and a printer control device 2090 that wholly controls the units and devices above.

It will be explained here with a direction along the longitudinal direction of the respective photosensitive drums as a Y-axis direction and a direction along the arranging direction of four photosensitive drums as an X-axis direction in an XYZ three-dimensional orthogonal coordinate system.

The communication control device 2080 controls bi-directional communication with an upper device (for example, a personal computer) via a network or the like.

The photosensitive drums are each formed with a photosensitive layer on its surface. More specifically, the surface of each of the photosensitive drums is a scanned surface. Each of the photosensitive drums rotates in an arrow direction on a plane indicated in FIG. 1 by a rotating mechanism not shown.

The charging device 2032a, the developing roller 2033a, and the cleaning unit 2031a are disposed near the surface of the photosensitive drum 2030a and along the rotating direction of the photosensitive drum 2030a.

The photosensitive drum 2030a, the charging device 2032a, the developing roller 2033a, the toner cartridge 2034a, and the cleaning unit 2031a are used as a set and constitute an image forming station that forms images in black (hereinafter, also referred to as "K station" for convenience sake).

The charging device 2032b, the developing roller 2033b, and the cleaning unit 2031b are disposed near the surface of the photosensitive drum 2030b and along the rotating direction of the photosensitive drum 2030b.

The photosensitive drum 2030b, the charging device 2032b, the developing roller 2033b, the toner cartridge 2034b, and the cleaning unit 2031b are used as a set and constitute an image forming station that forms images in cyan (hereinafter, also referred to as "C station" for convenience sake).

The charging device 2032c, the developing roller 2033c, and the cleaning unit 2031c are disposed near the surface of the photosensitive drum 2030c and along the rotating direction of the photosensitive drum 2030c.

The photosensitive drum 2030c, the charging device 2032c, the developing roller 2033c, the toner cartridge 2034c, and the cleaning unit 2031c are used as a set and constitute an image forming station that forms images in magenta (hereinafter, also referred to as "M station" for convenience sake).

The charging device 2032d, the developing roller 2033d, and the cleaning unit 2031d are disposed near the surface of the photosensitive drum 2030d and along the rotating direction of the photosensitive drum 2030d.

The photosensitive drum 2030d, the charging device 2032d, the developing roller 2033d, the toner cartridge 2034d, and the cleaning unit 2031d are used as a set and constitute an image forming station that forms images in yellow (hereinafter, also referred to as "Y station" for convenience sake).

Each of the charging devices charges the surface of the corresponding photosensitive drum evenly.

The light-scanning device 2010 irradiates the charged surfaces of the respective photosensitive drums with modulated light fluxes based on multi-color image information (black image information, cyan image information, magenta image information, and yellow image information) from the upper device. As a consequence, on each surface of the photosensitive drums, the electrical charges in the area that has been irradiated with light are lost, resulting in a formation of a latent image corresponding to the image information. The latent image thus formed moves in a direction towards the corresponding developing roller along with the rotation of the photosensitive drum. The structure of the light-scanning device 2010 will be described later.

The toner cartridge 2034a stores black toner therein and the black toner is supplied to the developing roller 2033a. The toner cartridge 2034b stores cyan toner therein and the cyan toner is supplied to the developing roller 2033b. The toner cartridge 2034c stores magenta toner therein and the magenta toner is supplied to the developing roller 2033c. The toner cartridge 2034d stores yellow toner therein and the yellow toner is supplied to the developing roller 2033d.

The toner from the corresponding toner cartridge is applied thinly and evenly on the surface of each developing roller along with the rotation of the developing roller. When the toner on the surface of each developing roller contacts the surface of the corresponding photosensitive drum, the toner is transferred and adhered only to the area that has been irradiated with light on the surface of the photosensitive drum. In other words, the developing roller elicits the latent image formed on the surface of the corresponding photosensitive drum with the toner adhered. The image with adhered toner (toner image) moves in a direction towards the transfer belt 2040 along with the rotation of the photosensitive drum.

The toner images in yellow, magenta, cyan, and black are transferred onto the transfer belt 2040 in sequence and are overlaid one on top of the other at designated timings to form a color image. The moving direction of the toner image on the transfer belt 2040 is referred to as "sub direction" and the direction orthogonally crossing the sub direction (Y-axis direction in this case) is referred to as "main direction".

The paper feed tray 2060 stores recording paper therein. The feed roller 2054 is disposed near the paper feed tray 2060. The feed roller 2054 takes out the recording paper from the paper feed tray 2060 one sheet at a time and conveys the recording paper to the registration roller pair 2056. The registration roller pair 2056 delivers the recording paper towards a gap formed between the transfer belt 2040 and the transfer roller 2042 at a designated timing. Consequently, the color image on the transfer belt 2040 is transferred onto the recording paper. The transferred recording paper is delivered to the fuser roller 2050.

With the fuser roller 2050, heat and pressure are applied to the recording paper so that the toner is fixed onto the recording paper. The fused recording paper is delivered to the catch tray 2070 via the delivery roller 2058 and is sequentially stacked in the catch tray 2070.

Each of the cleaning units removes the toner remained (residual toner) on the surface of the corresponding photosensitive drum. The surface of the photosensitive drum from which the residual toner has been removed returns to the position facing the corresponding charging device.

The toner pattern detector 2245 is disposed on a −X side of the transfer belt 2040 and outputs signals containing information regarding the position and the toner density of the detecting patterns on the transfer belt 2040. The toner pattern detector 2245 will be described later.

The structure of the light-scanning device 2010 will now be explained.

The light-scanning device 2010 includes, as illustrated in FIGS. 2 to 5 as an example, four light sources (2200a, 2200b, 2200c, and 2200d), four coupling lenses (2201a, 2201b, 2201c, and 2201d), four aperture plates (2202a, 2202b, 2202c, and 2202d), four cylindrical lenses (2204a, 2204b, 2204c, and 2204d), a polygon mirror 2104, four fθ lenses (2105a, 2105b, 2105c, and 2105d), eight reflecting mirrors (2106a, 2106b, 2106c, 2106d, 2108a, 2108b, 2108c, and 2108d), four toroidal lenses (2107a, 2107b, 2107c, and 2107d), four light-detecting sensors (2205a, 2205b, 2205c, and 2205d), four light-detecting mirrors (2207a, 2207b, 2207c, and 2207d), and a scanning control device not shown. These are mounted on an optical housing 2300 (omitted in FIGS. 2 to 4, see FIG. 5) at the appropriate locations.

In the following description, the direction corresponding to the main-scanning direction is abbreviated as "main-scanning corresponding direction" and the direction corresponding to the sub-scanning direction is abbreviated as "sub-scanning corresponding direction" for the sake of convenience.

The direction along the optical axes of the coupling lens 2201a and the coupling lens 2201b is defined as "w1 direction" and the main-scanning corresponding direction of the light source 2200a and the light source 2200b is defined as "m1 direction" for convenience sake. The direction along the optical axes of the coupling lens 2201c and the coupling lens 2201d is defined as "w2 direction" and the main-scanning corresponding direction of the light source 2200c and the light source 2200d is defined as "m2 direction". The sub-scanning corresponding direction of the light source 2200a and the light source 2200b and the sub-scanning corresponding direction of the light source 2200c and the light source 2200d are both in the same direction as the Z-axis direction.

The light source 2200b and the light source 2200c are disposed at positions apart from each other in the X-axis direction. The light source 2200a is disposed on a −Z side of the light source 2200b. The light source 2200d is disposed on the −Z side of the light source 2200c.

The coupling lens 2201a is disposed on the light path of the light flux output from the light source 2200a and forms the light flux into a substantially parallel light flux.

The coupling lens 2201b is disposed on the light path of the light flux output from the light source 2200b and forms the light flux into a substantially parallel light flux.

The coupling lens 2201c is disposed on the light path of the light flux output from the light source 2200c and forms the light flux into a substantially parallel light flux.

The coupling lens 2201d is disposed on the light path of the light flux output from the light source 2200d and forms the light flux into a substantially parallel light flux.

The aperture plate 2202a has an opening and shapes the light flux passing through the coupling lens 2201a.

The aperture plate 2202b has an opening and shapes the light flux passing through the coupling lens 2201b.

The aperture plate 2202c has an opening and shapes the light flux passing through the coupling lens 2201c.

The aperture plate 2202d has an opening and shapes the light flux passing through the coupling lens 2201d.

The cylindrical lens 2204a focuses the light flux passing through the opening of the aperture plate 2202a and forms an image near the deflecting reflective surface of the polygon mirror 2104 with respect to the Z-axis direction.

The cylindrical lens 2204b focuses the light flux passing through the opening of the aperture plate 2202b and forms an image near the deflecting reflective surface of the polygon mirror 2104 with respect to the Z-axis direction.

The cylindrical lens 2204c focuses the light flux passing through the opening of the aperture plate 2202c and forms an image near the deflecting reflective surface of the polygon mirror 2104 with respect to the Z-axis direction.

The cylindrical lens 2204d focuses the light flux passing through the opening of the aperture plate 2202d and forms an image near the deflecting reflective surface of the polygon mirror 2104 with respect to the Z-axis direction.

The polygon mirror 2104 has four-faceted mirrors in dual-stage structure and each of the mirrors serves as a deflecting reflective surface. The polygon mirror 2104 is arranged such that the light flux from the cylindrical lens 2204a and the light flux from the cylindrical lens 2204d are deflected with the four-faceted mirror of the first stage (lower stage) and the light flux from the cylindrical lens 2204b and the light flux from the cylindrical lens 2204c are deflected with the four-faceted mirror of the second stage (upper stage). The four-faceted mirror of the first stage and the four-faceted mirror of the second stage rotate with a phase difference of 45 degrees from each other and a write scan is carried out alternatively with the first stage and the second stage.

The light fluxes from the cylindrical lens 2204a and the cylindrical lens 2204b are deflected to the −X side of the polygon mirror 2104, and the light fluxes from the cylindrical lens 2204c and the cylindrical lens 2204d are deflected to the +X side of the polygon mirror 2104.

Each of the fθ lenses has an aspherical shape having refractive power such that the light spot moves on the surface of the corresponding photosensitive drum at a constant velocity in the main-scanning direction along with the rotation of the polygon mirror 2104.

The fθ lens 2105a and the fθ lens 2105b are disposed on the −X side of the polygon mirror 2104, and the fθ lens 2105c and the fθ lens 2105d are disposed on the +X side of the polygon mirror 2104.

Furthermore, the fθ lens 2105a and the fθ lens 2105b are stacked in the Z-axis direction, and the fθ lens 2105a is facing the four-faceted mirror of the first stage and the fθ lens 2105b is facing the four-faceted mirror of the second stage. The fθ lens 2105c and the fθ lens 2105d are stacked in the Z-axis direction, and the fθ lens 2105c is facing the four-faceted mirror of the second stage and the fθ lens 2105d is facing the four-faceted mirror of the first stage.

The photosensitive drum 2030a is irradiated with the light flux from the cylindrical lens 2204a deflected by the polygon mirror 2104 and passed through the fθ lens 2105a, the reflecting mirror 2106a, the toroidal lens 2107a, and the reflecting mirror 2108a, whereby a light spot is formed on the photosensitive drum 2030a. The light spot moves in the longitudinal direction of the photosensitive drum 2030a along with the rotation of the polygon mirror 2104. In other words, the light spot scans on the photosensitive drum 2030a. The moving direction of the light spot is the "main-scanning direction" of the photosensitive drum 2030a and the rotational direction of the photosensitive drum 2030a is the "sub-scanning direction" of the photosensitive drum 2030a.

The photosensitive drum 2030b is irradiated with the light flux from the cylindrical lens 2204b deflected by the polygon mirror 2104 and passed through the fθ lens 2105b, the reflecting mirror 2106b, the toroidal lens 2107b, and the reflecting mirror 2108b, whereby a light spot is formed on the photosensitive drum 2030. The light spot moves in the longitudinal direction of the photosensitive drum 2030b along with the rotation of the polygon mirror 2104. In other words, the light spot scans on the photosensitive drum 2030b. The moving direction of the light spot is the "main-scanning direction" of the photosensitive drum 2030b and the rotational direction of the photosensitive drum 2030b is the "sub-scanning direction" of the photosensitive drum 2030b.

The photosensitive drum 2030c is irradiated with the light flux from the cylindrical lens 2204c deflected by the polygon mirror 2104 and passed through the fθ lens 2105c, the reflecting mirror 2106c, the toroidal lens 2107c, and the reflecting mirror 2108c, whereby a light spot is formed on the photosensitive drum 2030c. The light spot moves in the longitudinal direction of the photosensitive drum 2030c along with the rotation of the polygon mirror 2104. In other words, the light spot scans on the photosensitive drum 2030c. The moving direction of the light spot is the "main-scanning direction" of the photosensitive drum 2030c and the rotational direction of the photosensitive drum 2030c is the "sub-scanning direction" of the photosensitive drum 2030c.

The photosensitive drum 2030d is irradiated with the light flux from the cylindrical lens 2204d deflected by the polygon mirror 2104 and passed through the fθ lens 2105d, the reflecting mirror 2106d, the toroidal lens 2107d, and the reflecting mirror 2108d, whereby a light spot is formed on the photosensitive drum 2030d. The light spot moves in the longitudinal direction of the photosensitive drum 2030d along with the rotation of the polygon mirror 2104. In other words, the light spot scans on the photosensitive drum 2030d. The moving direction of the light spot is the "main-scanning direction" of the photosensitive drum 2030d and the rotational direction of the photosensitive drum 2030d is the "sub-scanning direction" of the photosensitive drum 2030d.

The scanning area of each of the photosensitive drums in the main-scanning direction where image information is written is referred to as "effective scanning area" or "image forming area."

Each of the reflecting mirrors is disposed such that light paths leading from the polygon mirror 2104 to the respective photosensitive drums have the same length and that the photosensitive drums have the same incident positions and incident angles of the light fluxes.

The cylindrical lens and the corresponding toroidal lens thereof constitute an optical face tangle error correction system in which the deflection point and the surface of the corresponding photosensitive drum are arranged in a conjugate relationship in the sub-scanning direction.

The optical systems disposed in the light paths between the polygon mirror 2104 and the respective photosensitive drums are also referred to as scanning optical systems. In the present embodiment, the fθ lens 2105a, the toroidal lens 2107a, and the reflecting mirrors (2106a and 2108a) constitute the scanning optical system for the K station. The fθ lens 2105b, the toroidal lens 2107b, and the reflecting mirrors (2106b and 2108b) constitute the scanning optical system for the C station. The fθ lens 2105c, the toroidal lens 2107c, and the reflecting mirrors (2106c and 2108c) constitute the scanning optical system for the M station. The fθ lens 2105d, the toroidal lens 2107d, and the reflecting mirrors (2106d and 2108d) constitute the scanning optical system for the Y station.

The light-detecting sensor 2205a receives via the light-detecting mirror 2207a a part of the light flux before writing that is deflected by the polygon mirror 2104 and passed through the scanning optical system for the K station.

The light-detecting sensor 2205b receives via the light-detecting mirror 2207b a part of the light flux before writing that is deflected by the polygon mirror 2104 and passed through the scanning optical system for the C station.

The light-detecting sensor 2205c receives via the light-detecting mirror 2207c a part of the light flux before writing that is deflected by the polygon mirror 2104 and passed through the scanning optical system for the M station.

The light-detecting sensor 2205d receives via the light-detecting mirror 2207d a part of the light flux before writing that is deflected by the polygon mirror 2104 and passed through the scanning optical system for the Y station.

Each of the light-detecting sensors outputs a signal (photoelectric conversion signal) according to the amount of light received.

The scanning control device detects a start timing of scanning for each of the photosensitive drums based on the output signal of the corresponding light-detecting sensor.

The toner pattern detector 2245 will now be explained.

Figure 6:
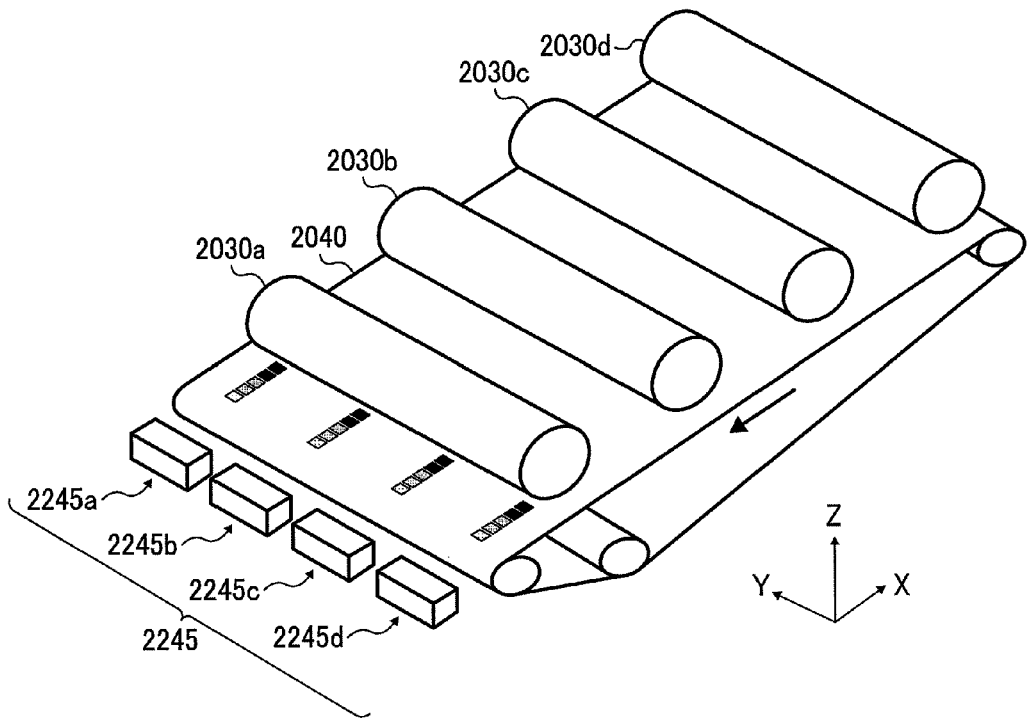
FIG. 6 is a schematic for explaining a toner pattern detector illustrated in FIG. 1.

The toner pattern detector 2245 has four reflective optical sensors (2245a, 2245b, 2245c, and 2245d) as illustrated in FIG. 6 as an example.

The reflective optical sensor 2245a is disposed in a position facing the area near the +Y side-end of the transfer belt 2040, and the reflective optical sensor 2245d is disposed in a position facing the area near the −Y side-end of the transfer belt 2040. The reflective optical sensor 2245b is disposed on the −Y side of the reflective optical sensor 2245a, while the reflective optical sensor 2245c is disposed on the +Y side of the reflective optical sensor 2245d. The reflective optical sensor 2245b and the reflective optical sensor 2245c are disposed such that the distance between the neighboring reflective optical sensors is nearly equal with respect to the Y-axis direction.

Figure 7:
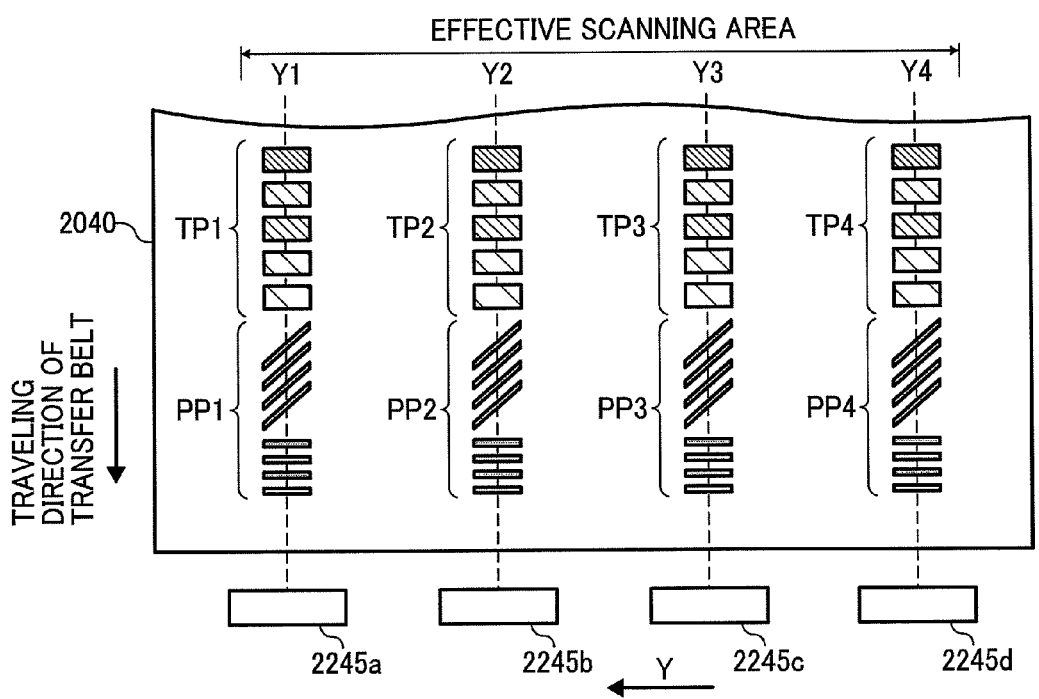
FIG. 7 is a schematic for explaining the arrangement of reflective optical sensors.

As illustrated in FIG. 7 as an example, with respect to the Y-axis direction, the center position of the reflective optical sensor 2245a is defined as Y1, the center position of the reflective optical sensor 2245b is defined as Y2, the center position of the reflective optical sensor 2245c is defined as Y3, and the center position of the reflective optical sensor 2245d is defined as Y4 here.

The toner patterns facing the reflective optical sensor 2245a are defined as PP1 and TP1, the toner patterns facing the reflective optical sensor 2245b are defined as PP2 and TP2, the toner patterns facing the reflective optical sensor 2245c are defined as PP3 and TP3, and the toner patterns facing the reflective optical sensor 2245d are defined as PP4 and TP4.

The toner patterns PP1, PP2, PP3, and PP4 are position detecting patterns and the toner patterns TP1, TP2, TP3, and TP4 are density detecting patterns.

The position detecting patterns PP1, PP2, PP3, and PP4 have the same structure. Accordingly they are also collectively referred to as "position detecting pattern PP" below when it is not necessary to distinguish the position detecting patterns.

Figure 8:
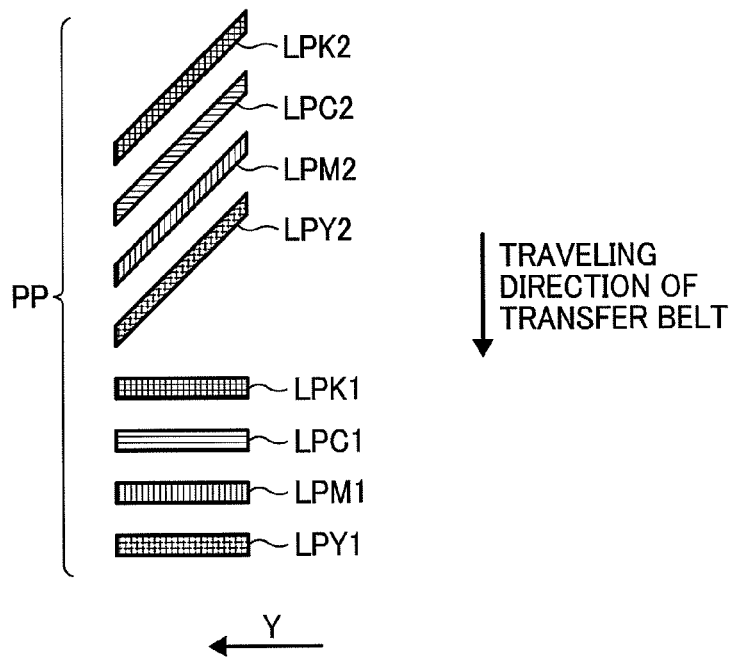
FIG. 8 is a schematic for explaining position detecting patterns.

The position detecting pattern PP, as illustrated in FIG. 8, is configured with four line-shape patterns (LPY1, LPM1, LPC1, and LPK1) parallel to the main direction (Y-axis direction) and four line-shape patterns (LPY2, LPM2, LPC2, and LPK2) inclined with respect to the main direction.

The line-shape patterns LPY1 and LPY2 make up a pair and are formed with yellow toner, the line-shape patterns LPM1 and LPM2 make up a pair and are formed with magenta toner, the line-shape patterns LPC1 and LPC2 make up a pair and are formed with cyan toner, and the line-shape patterns LPK1 and LPK2 make up a pair and are formed with black toner.

Each pair of line-shape patterns is arranged such that the distance between the two line-shape patterns is of a predetermined distance with respect to the traveling direction of the transfer belt 2040.

The density detecting patterns TP1 are formed with yellow toner, the density detecting patterns TP2 are formed with magenta toner, the density detecting patterns TP3 are formed with cyan toner, and the density detecting patterns TP4 are formed with black toner. They are also collectively referred to as "density detecting pattern TP" below when it is not necessary to distinguish the density detecting patterns.

Figure 9:
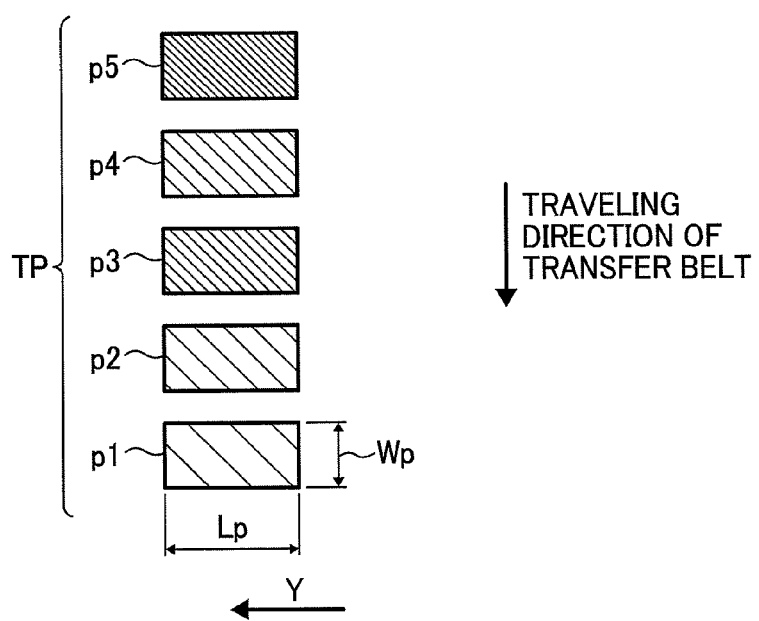
FIG. 9 is a schematic for explaining density detecting patterns.

The density detecting pattern TP, as illustrated in FIG. 9 as an example, has a pattern including five rectangles (p1 to p5, hereinafter referred to as "rectangular patterns" for convenience sake). The rectangular patterns are lined up in a single row along the traveling direction of the transfer belt 2040 and each has a toner density of different gradation when viewed as a whole. The rectangular patterns here are defined as p1, p2, p3, p4, and p5 from the lower toner density. In other words, the rectangular pattern p1 has the lowest toner density and the rectangular pattern p5 has the highest toner density.

The length of each rectangular pattern in the Y-axis direction is defined as Lp and the length in the traveling direction of the transfer belt 2040 is defined as Wp. The Lp here is set to 1.0 millimeter.

The gradation of the toner density can be changed by the adjustment of power of the light flux output from the light source, the adjustment of duty of the drive pulse supplied to the light source, and the adjustment of developing bias.

They are collectively referred to as "toner patterns" below when it is not necessary to distinguish the position detecting patterns and the density detecting pattern.

The printer control device 2090 instructs the scanning control device to form the position detecting patterns and the density detecting patterns when carrying out the position detecting process and the density detecting process using the toner pattern detector 2245.

Figure 10:
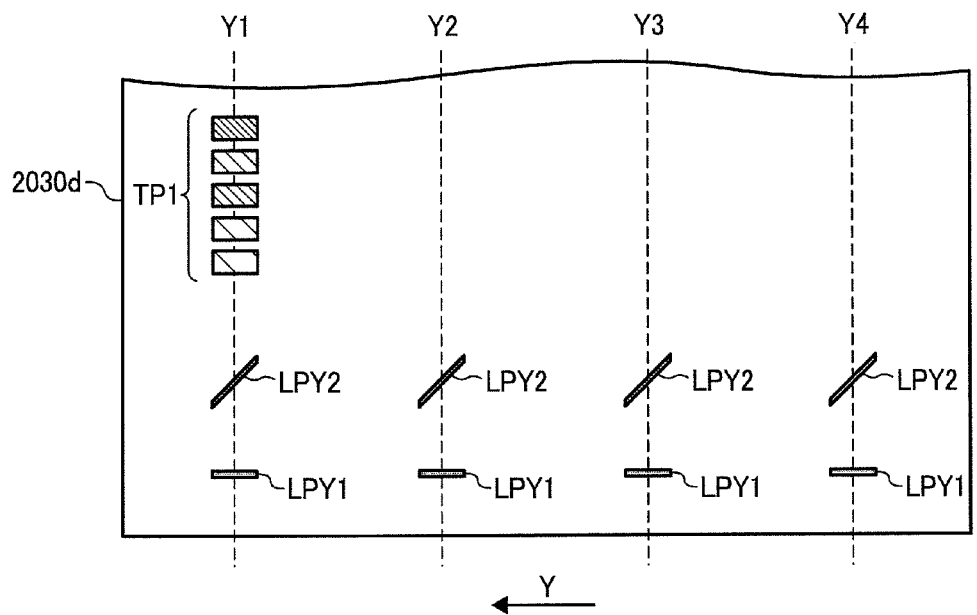
FIG. 10 is a schematic for explaining the forming of toner patterns in a Y station.

The scanning control device controls the Y station such that the line-shape patterns LPY1 and LPY2 are formed at the locations Y1, Y2, Y3, and Y4 and that the density detecting patterns TP1 are formed at the location Y1 on the photosensitive drum 2030d (see FIG. 10).

Figure 11:
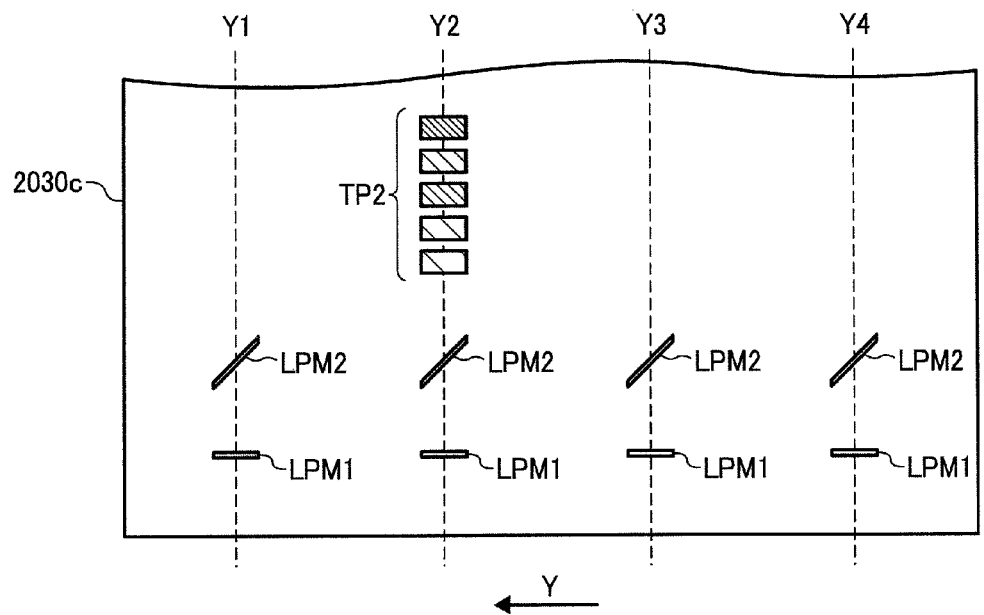
FIG. 11 is a schematic for explaining the forming of toner patterns in an M station.

The scanning control device controls the M station such that the line-shape patterns LPM1 and LPM2 are formed at the locations Y1, Y2, Y3, and Y4 and that the density detecting patterns TP2 are formed at the location Y2 on the photosensitive drum 2030c (see FIG. 11).

Figure 12:
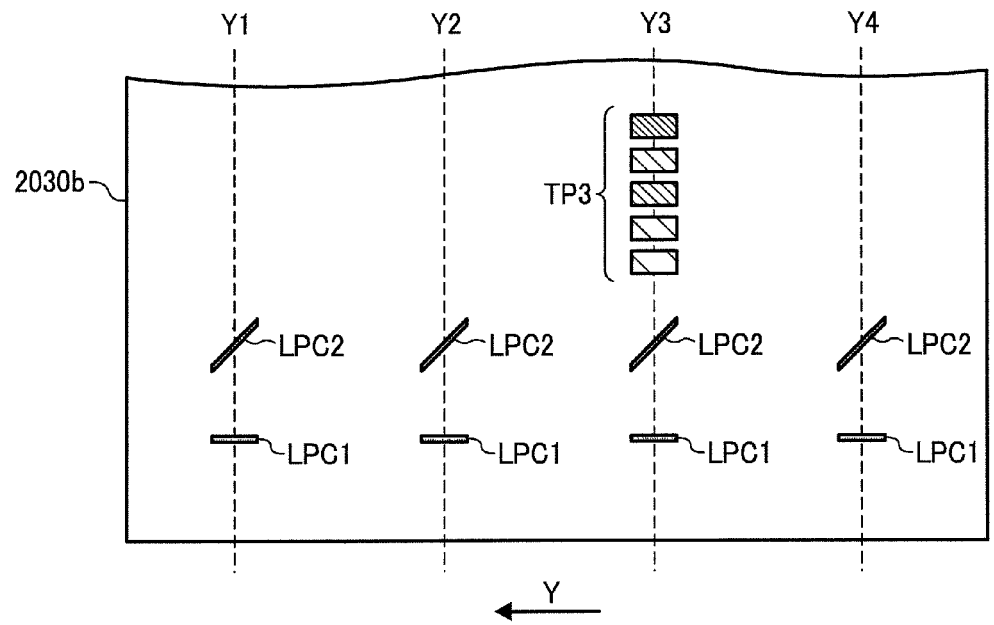
FIG. 12 is a schematic for explaining the forming of toner patterns in a C station.

The scanning control device controls the C station such that the line-shape patterns LPC1 and LPC2 are formed at the locations Y1, Y2, Y3, and Y4 and that the density detecting patterns TP3 are formed at the location Y3 on the photosensitive drum 2030b (see FIG. 12).

Figure 13:
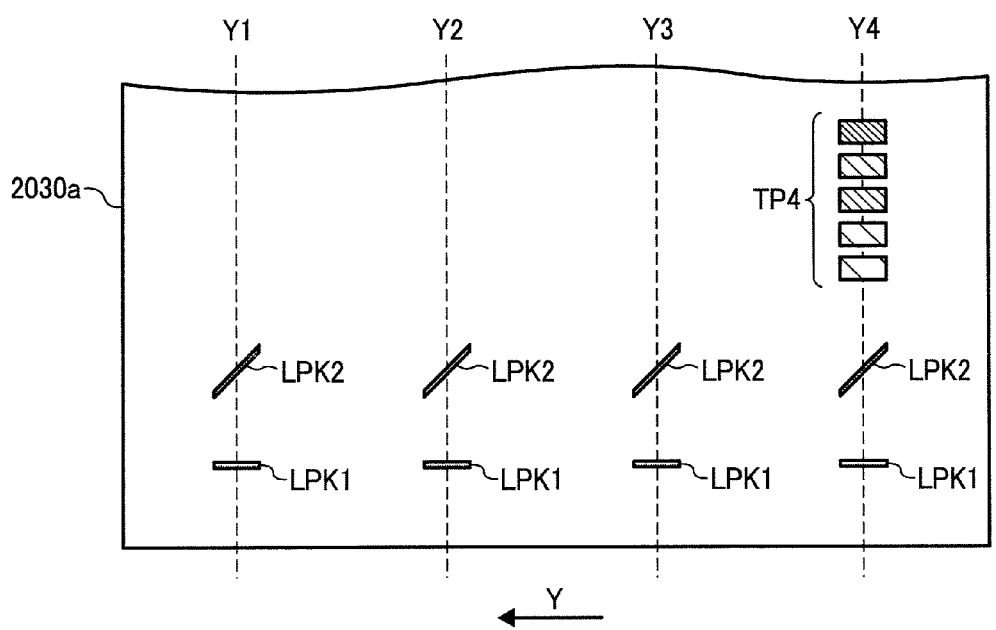
FIG. 13 is a schematic for explaining the forming of toner patterns in a K station.

The scanning control device controls the K station such that the line-shape patterns LPK1 and LPK2 are formed at the locations Y1, Y2, Y3, and Y4 and that the density detecting patterns TP4 are formed at the location Y4 on the photosensitive drum 2030a (see FIG. 13).

The line-shape patterns LPY1 and LPY2 and the density detecting patterns TP1 formed by the Y station are transferred to the transfer belt 2040 at a designated timing.

The line-shape patterns LPM1 and LPM2 and the density detecting patterns TP2 formed by the M station are transferred to the transfer belt 2040 at a designated timing.

The line-shape patterns LPC1 and LPC2 and the density detecting patterns TP3 formed by the C station are transferred to the transfer belt 2040 at a designated timing.

The line-shape patterns LPK1 and LPK2 and the density detecting patterns TP4 formed by the K station are transferred to the transfer belt 2040 at a designated timing.

Figure 14:
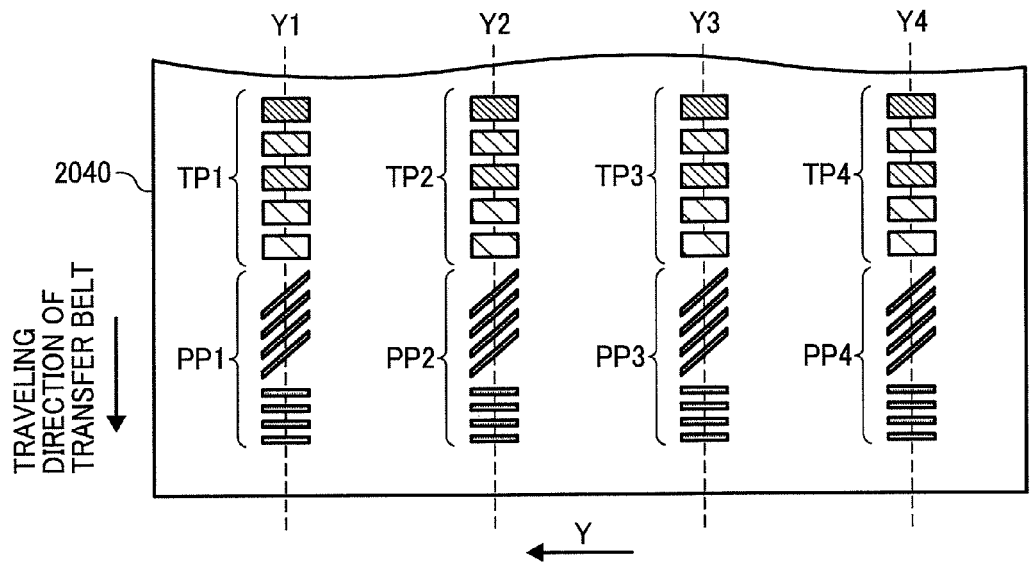
FIG. 14 is a schematic for explaining toner patterns transferred to a transfer belt.

As a result, the position detecting patterns and the density detecting patterns are formed at the locations Y1, Y2, Y3, and Y4 on the transfer belt 2040 (see FIG. 14).

All of the four reflective optical sensors (2245a, 2245b, 2245c, and 2245d) have the same configuration and structure. Hence, the configuration and structure of the reflective optical sensor will be explained below with the reflective optical sensor 2245a as an example.

Figure 15:
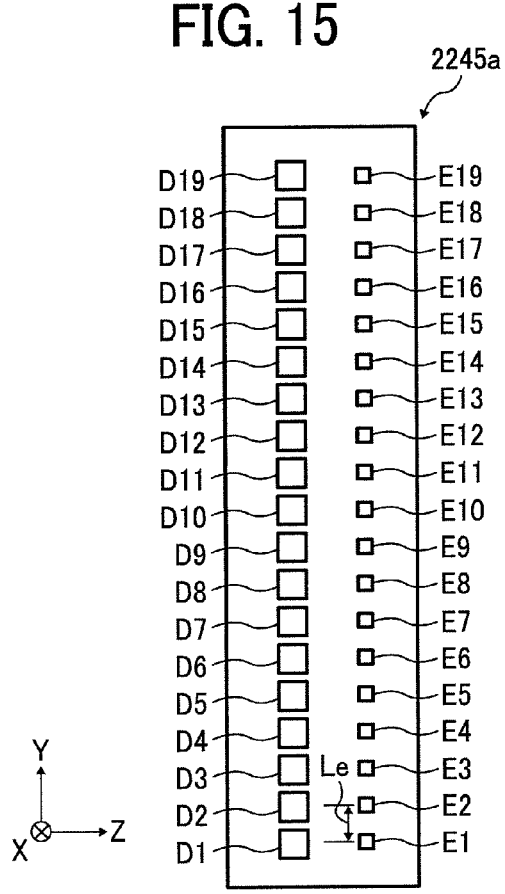
FIG. 15 is a schematic for explaining a reflective optical sensor (part 1)
Figure 16:
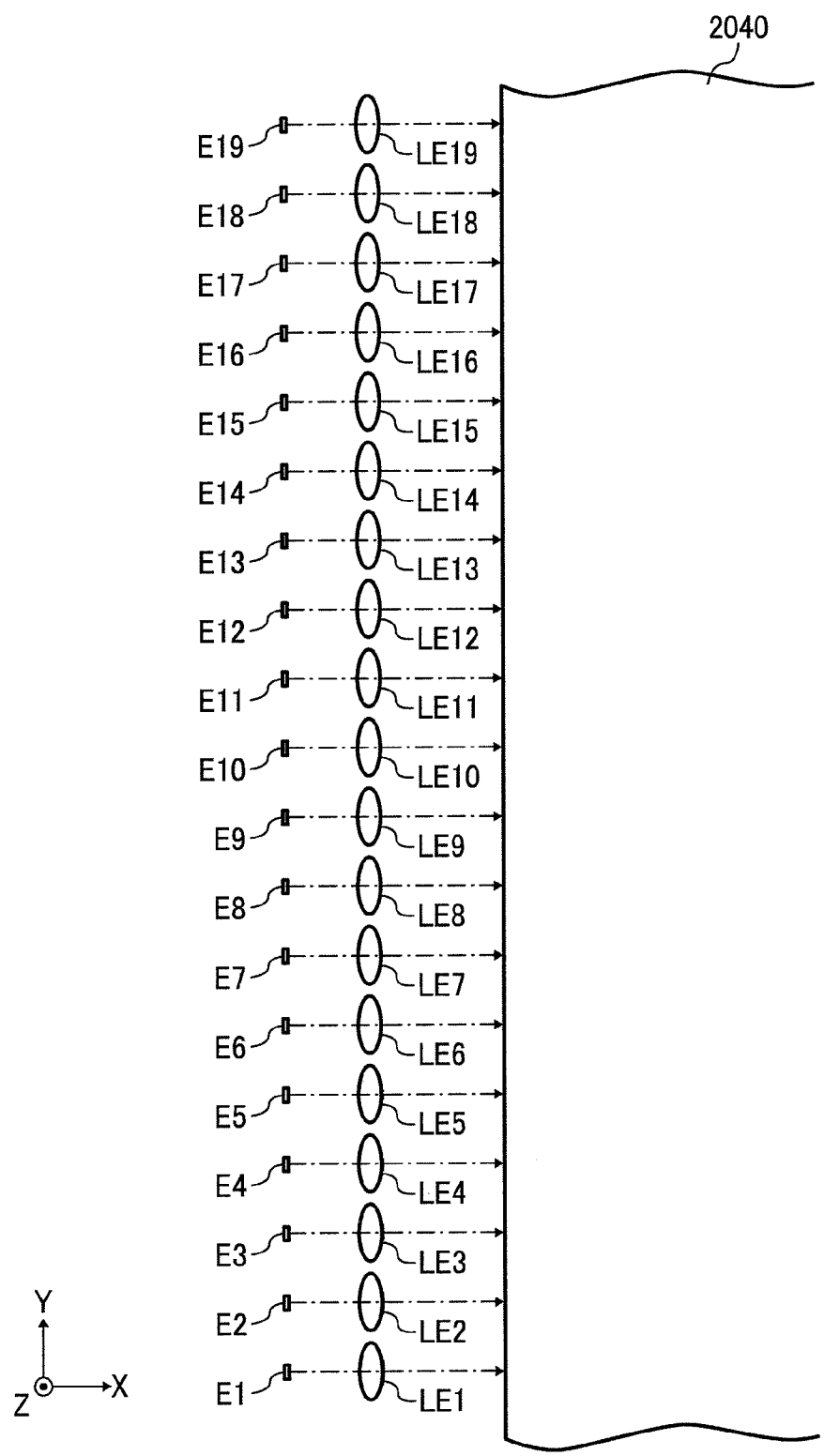
FIG. 16 is a schematic for explaining the reflective optical sensor (part 2)

The reflective optical sensor 2245a, as illustrated in FIGS. 15 and 16 as an example, includes an illuminating system including 19 pieces of light-emitting units (E1 to E19), an illuminating optical system including 19 pieces of illuminating condenser lenses (LE1 to LE19), a light-receiving system including 19 pieces of light-receiving units (D1 to D19), and a processor not shown.

The 19 pieces of light-emitting units (E1 to E19) are disposed along the Y-axis at an equal distance Le. A light-emitting diode (LED) can be used for each light-emitting unit. As an example, Le here is set to 0.4 millimeter. The light-emitting plane of each of the light-emitting units is in parallel with the Y-Z plane.

The 19 pieces of illuminating condenser lenses (LE1 to LE19) correspond to the respective 19 pieces of light-emitting units (E1 to E19). As an example, the size of each illuminating condenser lens here is 0.4 millimeter in diameter.

Each of the illuminating condenser lenses is disposed on the +X side of the corresponding light-emitting unit, and guides the light flux output from the light-emitting unit to the surface of the transfer belt 2040.

Figure 17:
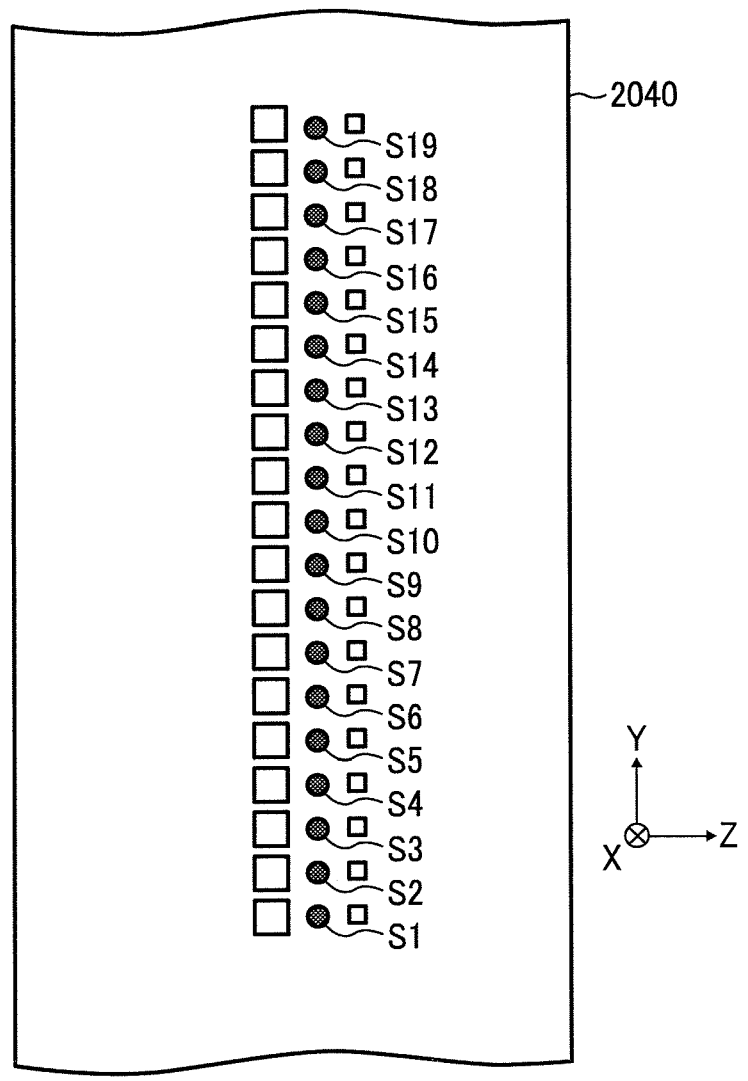
FIG. 17 is a schematic for explaining light detection.

To make the explanation easier to understand, the transfer belt 2040 is to be irradiated only with the light fluxes output from the light-emitting units and passed through the corresponding illuminating condenser lenses, the light fluxes each serving as the detecting light (S1 to S19) (see FIG. 17).

The optical axis of each of the illuminating condenser lenses is parallel to a direction orthogonally crossing the light-emitting plane of the corresponding light-emitting unit (X-axis in this case).

The surface of the transfer belt 2040 is smooth, and most of the detecting light incident on the surface of the transfer belt 2040 reflects regularly.

As an example, the size of the light spot of the detecting light formed on the transfer belt 2040 is 0.2 millimeter in diameter. The size of the light spot of a conventional detecting light is about 2 to 3 millimeters in diameter.

For the illuminating condenser lens, for example, a spherical lens having a light-focusing function with respect to the Y-axis direction and Z-axis direction, a cylindrical lens having positive refractive power with respect to the Z-axis direction, and an anamorphic lens having refractive power with respect to the Y-axis direction and refractive power with respect to the Z-axis direction different from each other can be used.

Returning back to FIG. 15, the light-receiving units (D1 to D19) correspond to the respective light-emitting units (E1 to E19).

Each light-receiving unit is disposed on the −Z side of the corresponding light-emitting unit and on the light path of the light flux output from the light-emitting unit and regularly reflected on the surface of the transfer belt 2040. In other words, the arrangement pitch of the 19 pieces of light-receiving units is equal to the arrangement pitch of the 19 pieces of light-emitting units.

Each of the light-receiving units is arranged so as to receive only the regularly reflected light of the corresponding detecting light when the surface of the transfer belt 2040 is irradiated with the detecting light from the corresponding light-emitting unit.

A photo diode (PD) can be used for the light-receiving unit. Each of the light-receiving units outputs a signal in response to the amount of light received.

When it is not necessary to specify the light-emitting unit, the light-emitting units are represented as a light-emitting unit Ei. The illuminating condenser lens corresponding to the light-emitting unit Ei is represented as an illuminating condenser lens LEi. The light flux output from the light-emitting unit Ei and passed through the illuminating condenser lens LEi is represented as detecting light Si. The light-receiving unit corresponding to the light-emitting unit Ei is represented as a light-receiving unit Di.

Figure 18:
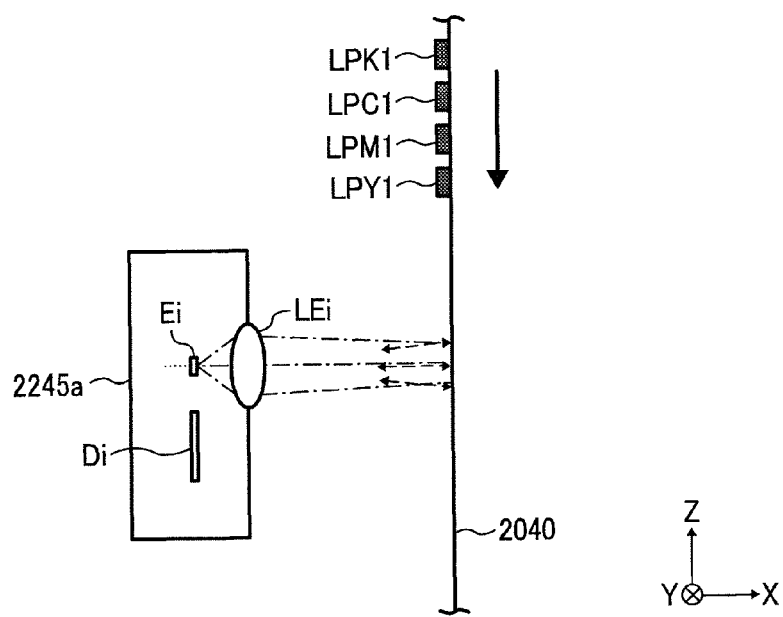
FIG. 18 is a schematic for explaining an illuminating condenser lens (part 1)

Meanwhile, when the optical axis of the illuminating condenser lens LEi and an axis passing through a center of and orthogonally crossing the light-emitting plane of the light-emitting unit Ei coincide with each other, as illustrated in FIG. 18, the light flux output from the light-emitting unit Ei and passed through the illuminating condenser lens LEi may become nearly parallel to the optical axis of the illuminating condenser lens LEi. In this case, the majority of the light flux reflected by the transfer belt 2040 does not reach the light-receiving unit Di. Consequently, the difference in reflective characteristics between the transfer belt 2040 and the toner patterns becomes small, thereby deteriorating the detection accuracy of pattern position and toner density.

Figure 19:
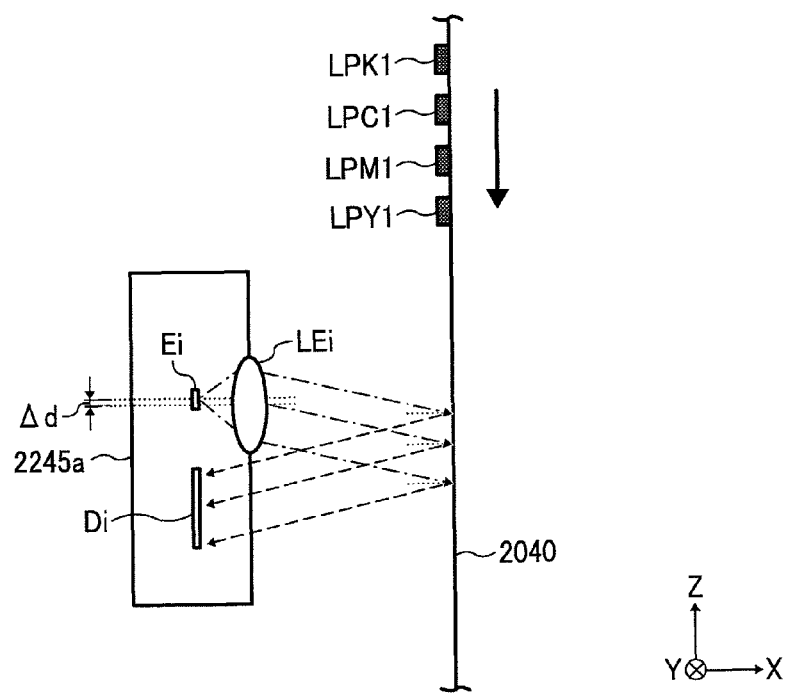
FIG. 19 is a schematic for explaining the illuminating condenser lens (part 2)

In the present embodiment, as illustrated in FIG. 19 as an example, the optical axis of the illuminating condenser lens LEi is off-center to the −Z direction by the amount of Δd to make the light flux passed through the illuminating condenser lens LEi inclined with respect to the optical axis of the illuminating condenser lens LEi. When the illuminating condenser lens LEi is thus disposed, the light flux reflected by the transfer belt 2040 is guided towards the light-receiving unit Di. As an example, the off-center amount Δd of the illuminating condenser lens LEi here is set to about 10% of the diameter of the illuminating condenser lens LEi, i.e., about 0.04 millimeter.

It is desirable that the center of the detecting light spot on the transfer belt 2040 and on the toner patterns lies about halfway between the light-emitting unit and the light-receiving unit with respect to the Z-axis direction.

Figure 20:
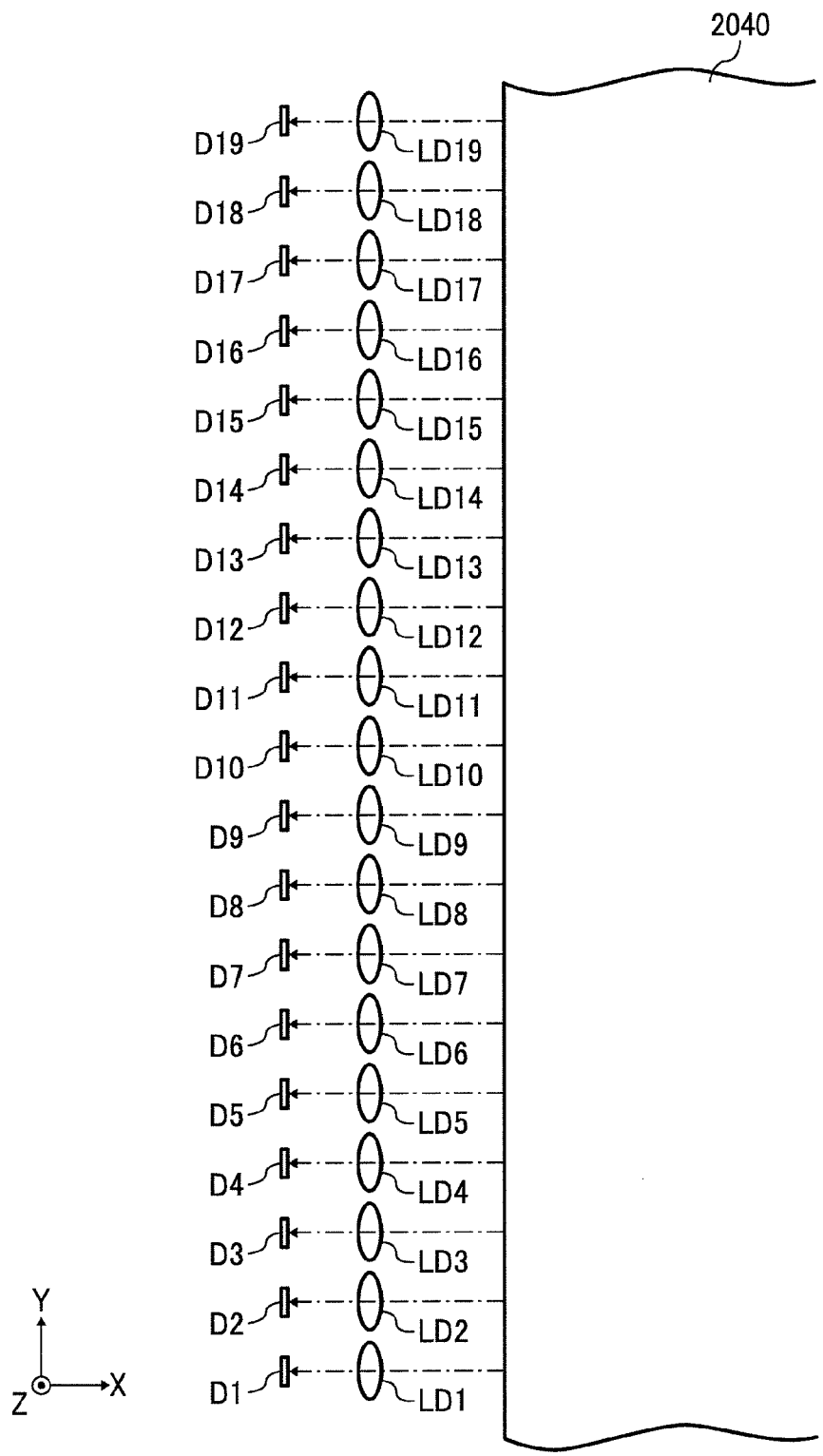
FIG. 20 is a schematic for explaining a light-receiving condenser lens (part 1)

As illustrated in FIG. 20 as an example, a light-receiving optical system including 19 pieces of light-receiving condenser lenses (LD1 to LD19) that corresponds to the respective 19 pieces of light-receiving units (D1 to D19) and that focus the detecting light reflected by the transfer belt 2040 or by the toner patterns may further be provided. In this case, the amount of light received by each of the light-receiving units can be increased. In other words, the detecting sensitivity is enhanced. The light-receiving planes of the respective light-receiving units are parallel to the Y-Z plane here.

Figure 21:
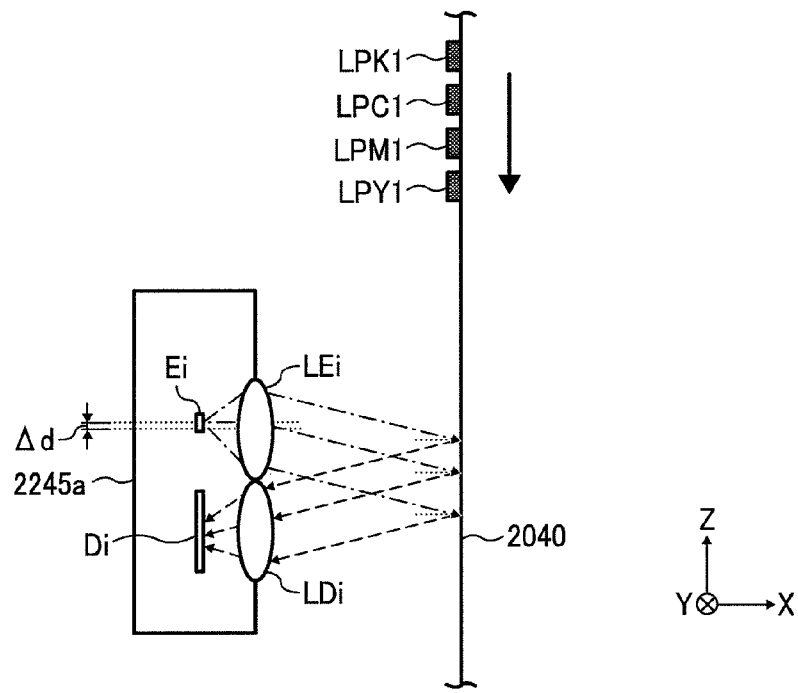
FIG. 21 is a schematic for explaining the light-receiving condenser lens (part 2)

The light-receiving condenser lens corresponding to the light-receiving unit Di is represented as a light-receiving condenser lens LDi (see FIG. 21).

The optical axis of the light-receiving condenser lens LDi is parallel to the X-axis direction. In FIGS. 20 and 21, the optical axis of the light-receiving condenser lens LDi coincides with the axis passing through the center of and orthogonally crossing the light-receiving plane of the light-receiving unit Di.

The degree of light condensation of the light flux passed through the illuminating condenser lens LEi can be changed by altering the thickness, the shape, the refraction index, or the like of the illuminating condenser lens LEi.

Figure 22:
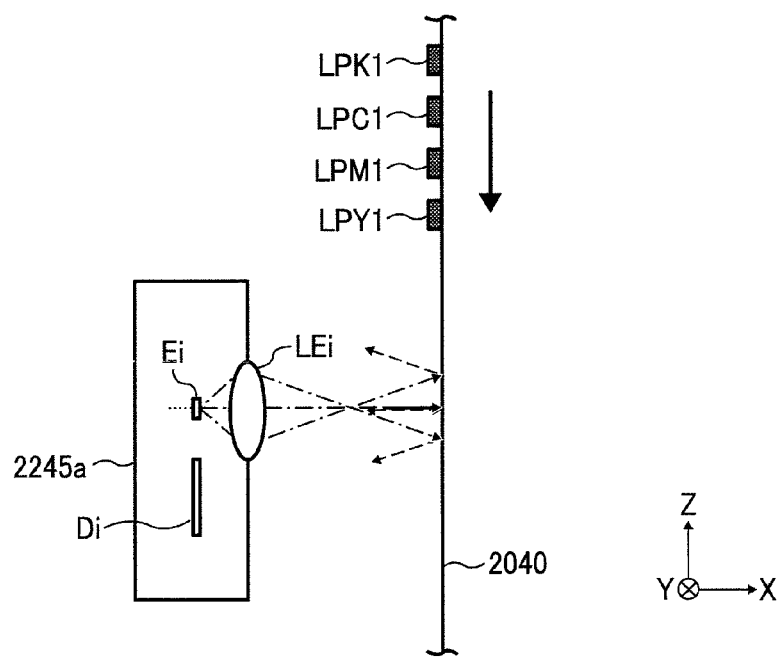
FIG. 22 is a schematic for explaining a modification example of an illuminating condenser lens.

FIG. 22 depicts the light flux output from the light-emitting unit Ei becoming convergent light after passing through the illuminating condenser lens LEi and becoming diverging light before being incident on the transfer belt 2040 when the optical axis of the illuminating condenser lens LEi coincides with the axis passing through the center of and orthogonally crossing the light-emitting plane of the light-emitting unit Ei. In this case, even though the light beam reaching the light-receiving unit Di is increased compared with when the light flux passing through the illuminating condenser lens LEi is nearly parallel with the optical axis of the illuminating condenser lens LEi (see FIG. 18), the majority of light flux reflected by the transfer belt 2040 does not reach the light-receiving unit Di.

Figure 23:
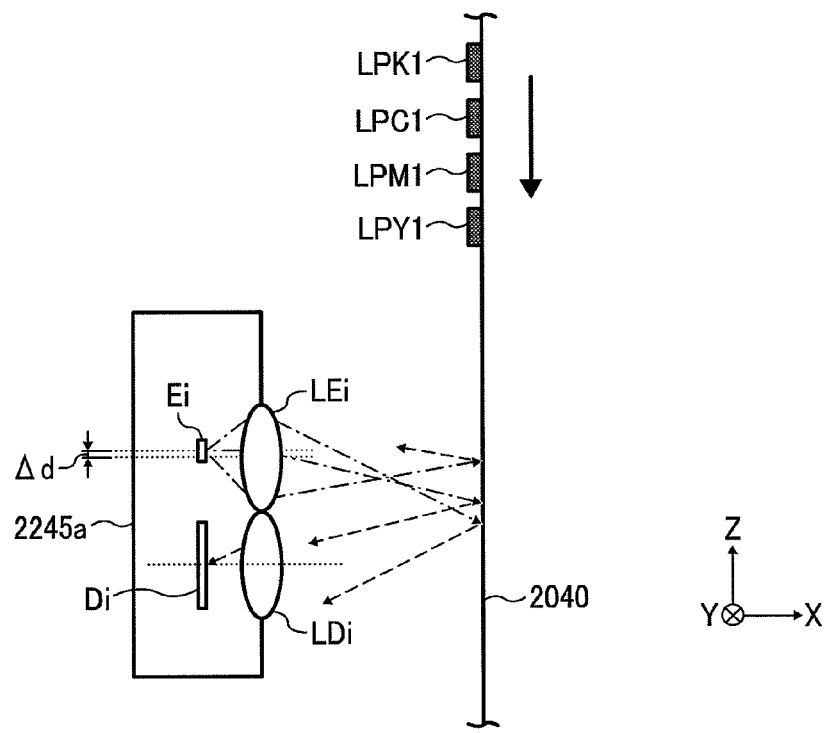
FIG. 23 is a schematic for explaining the illuminating condenser lens being off-center.

Accordingly, as illustrated in FIG. 23 as an example, further providing a light-receiving optical system and making the optical axis of the illuminating condenser lens LEi off-center towards the −Z direction by the amount of Δd make it possible for a part of the detecting light Si reflected by the transfer belt 2040 or the toner patterns to reach the light-receiving unit Di. Even in this case, a part of the light beam not reaching the light-receiving unit Di still remains.

Figure 24:
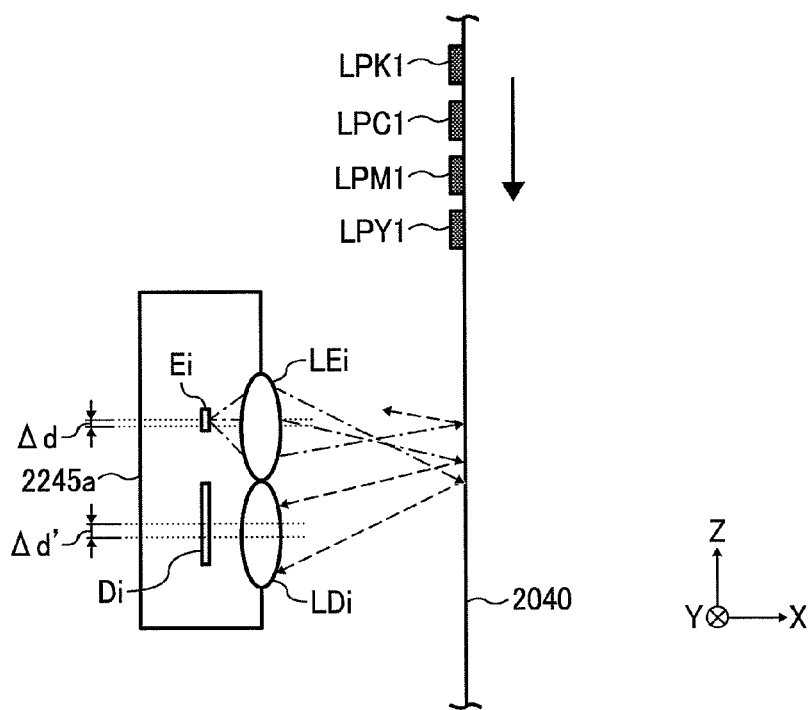
FIG. 24 is a schematic for explaining the light-receiving condenser lens being off-center.

In this case, as illustrated in FIG. 24 as an example, further making the light-receiving condenser lens LDi off-center towards the −Z direction by the amount of Δd' makes more light beam be condensed and guided to the light-receiving unit Di by the light-receiving condenser lens LDi.

Figure 25:
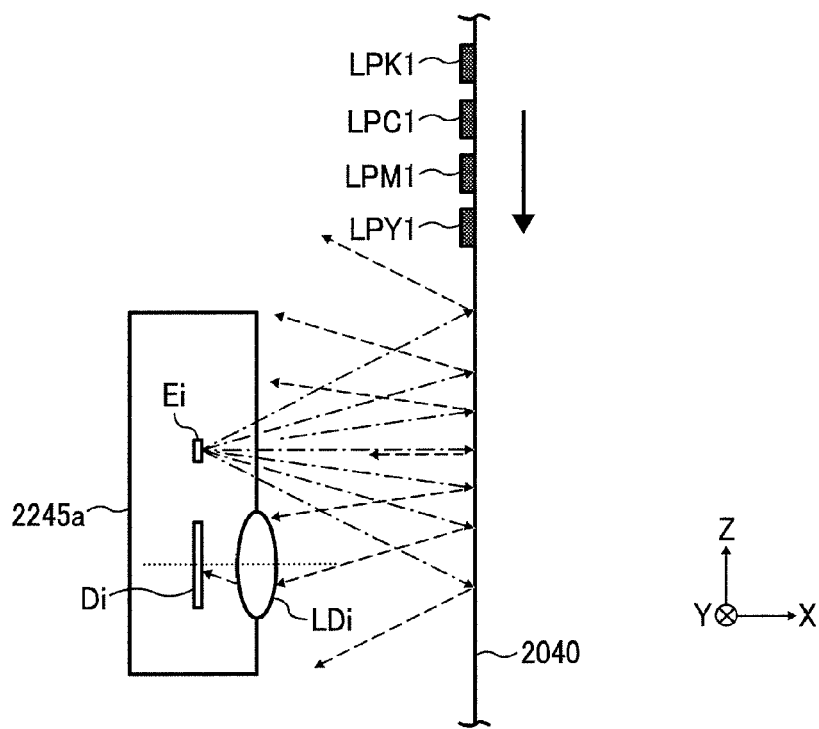
FIG. 25 is a schematic for explaining a modification example of a reflective optical sensor.

As a modification example of the reflective optical sensor 2245a, as illustrated in FIG. 25, a reflective optical sensor that includes a light-receiving optical system but does not include an illuminating optical system is conceivable.

Even in this case, when the optical axis of the light-receiving condenser lens LDi coincides with the axis passing through the center of and orthogonally crossing the light-receiving plane of the light-receiving unit Di, although a part of the detecting light Si reflected by the transfer belt 2040 or the toner patterns is condensed and guided to the light-receiving unit Di by the light-receiving condenser lens LDi, the amount of light beam guided is small.

Generally, an LED and a laser diode (LD) used for the light-emitting unit Ei have directional characteristics. More specifically, in the light beam output from the LED and the LD, the smaller inclined angle with respect to the direction perpendicular to the light-emitting plane of the LED and the LD is directly related to the larger light intensity. Accordingly, when condensing the light beam with the light-receiving condenser lens LDi, it is more efficient to condense more of the light beam having a smaller inclined angle with respect to the direction perpendicular to the light-emitting plane of the light-emitting unit Ei and guide the light beam to the light-receiving unit Di.

Figure 26:
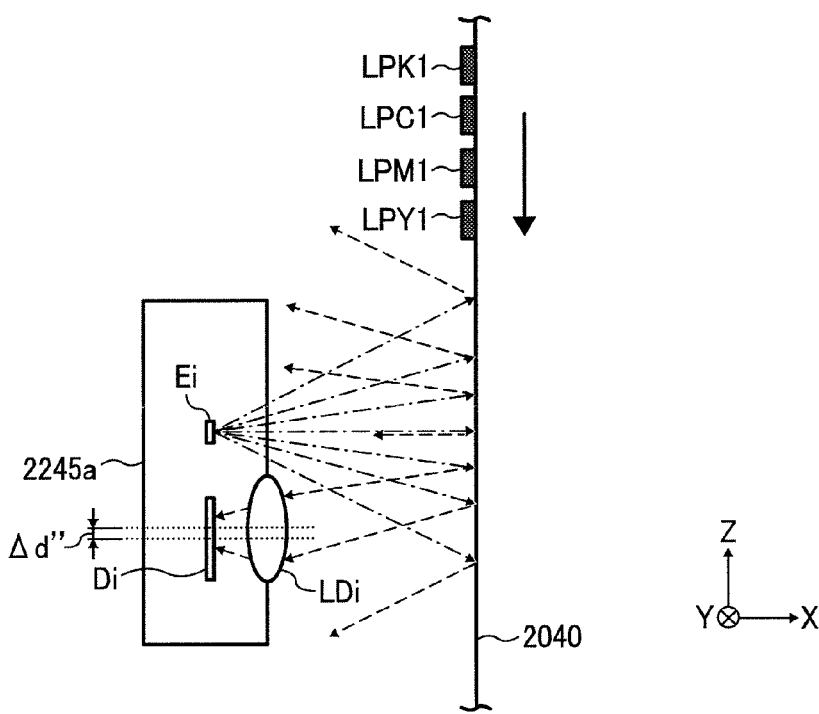
FIG. 26 is a schematic for explaining the light-receiving condenser lens being off-center.

In this case, as illustrated in FIG. 26 as an example, making the light-receiving condenser lens LDi off-center towards the +Z direction by the amount of Δd'' makes it possible to condense the light beam having a higher light intensity and guide the light beam to the light-receiving unit Di with the light-receiving condenser lens LDi.

Figure 27:
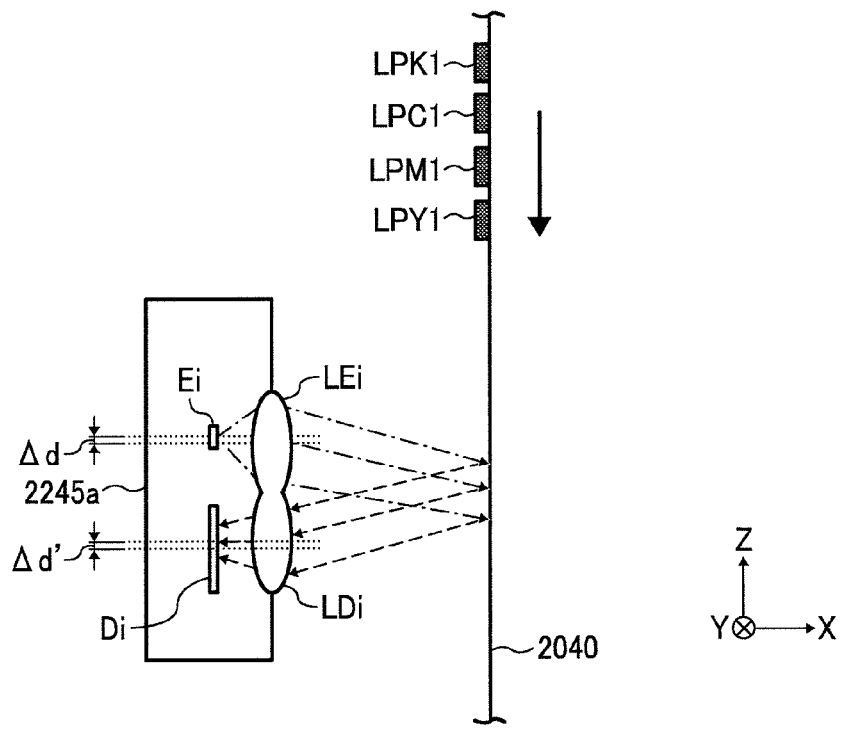
FIG. 27 is a schematic for explaining condenser lenses being off-center.
Figure 28:
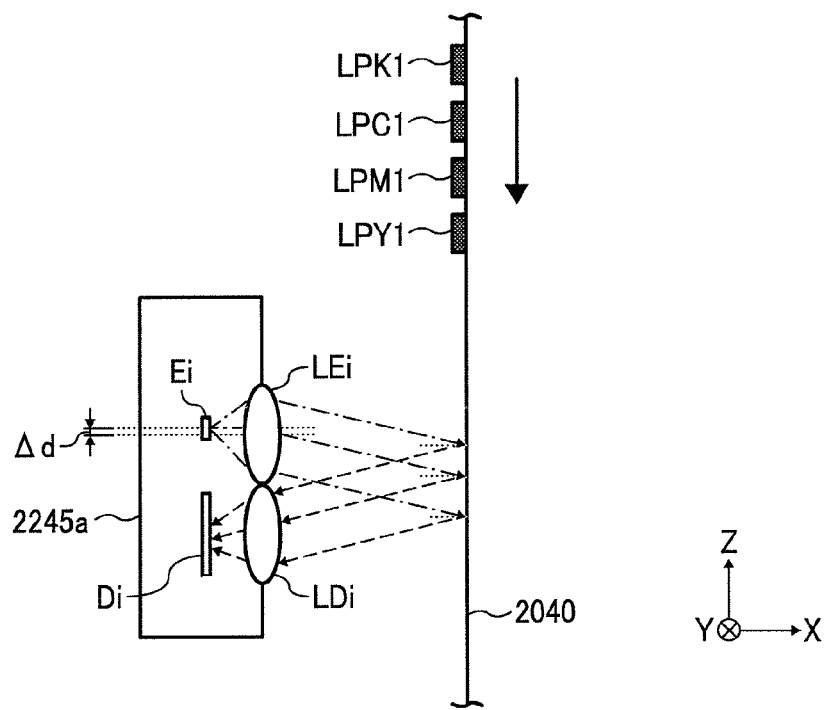
FIG. 28 is a schematic for explaining a modification example of condenser lenses (part 1)
Figure 29:
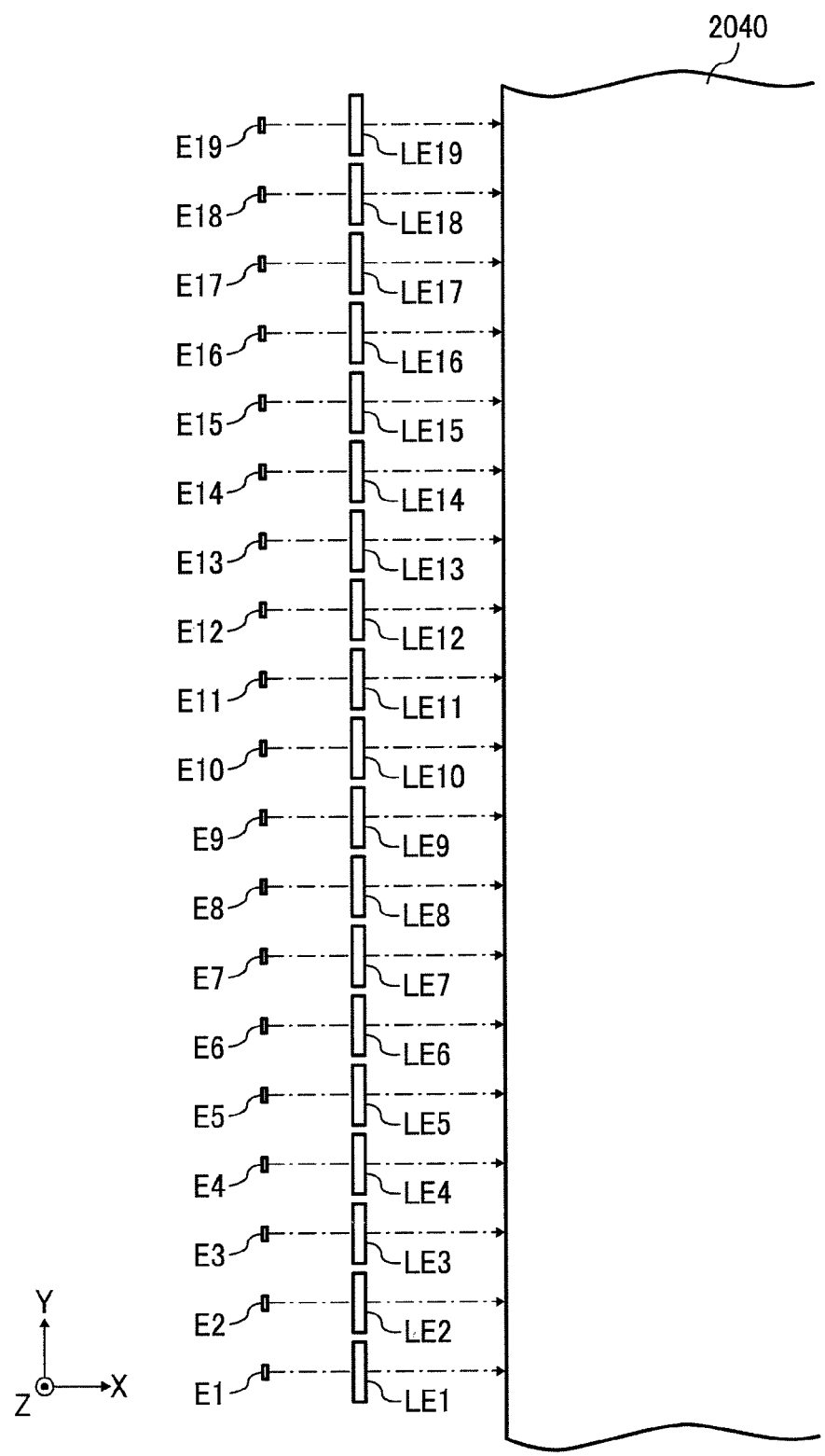
FIG. 29 is a schematic for explaining the modification example of the condenser lenses (part 2)
Figure 30:
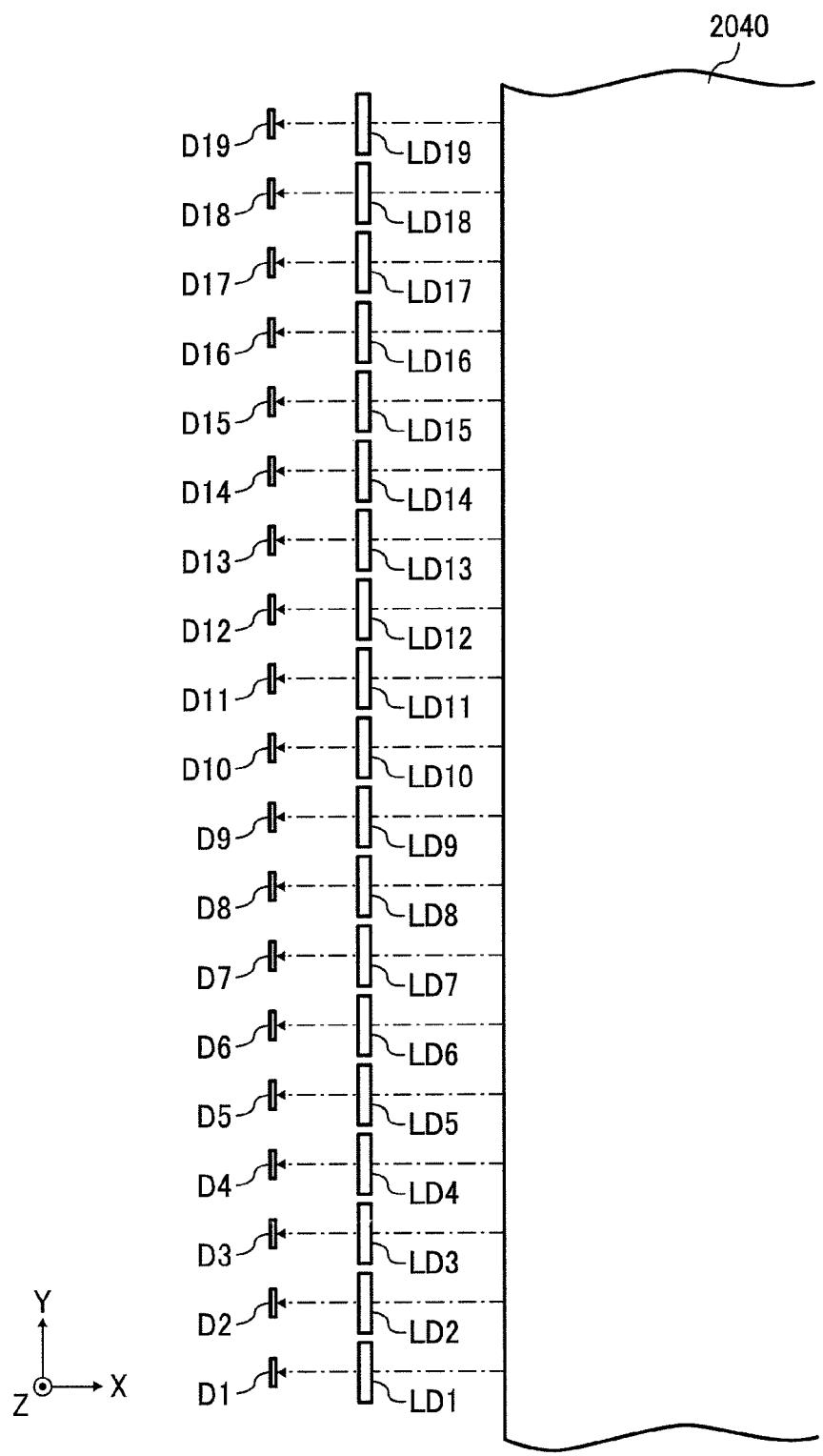
FIG. 30 is a schematic for explaining the modification example of the condenser lenses (part 3)

In this case, as illustrated in FIG. 27 as an example, an illuminating optical system may further be provided and the illuminating optical system may be integrated with the light-receiving optical system. The integration allows mounting accuracy to be improved.

At least one of the illuminating condenser lens LEi or light-receiving condenser lens LDi may be a spherical lens having refractive power in the Y-axis direction and in the Z-axis direction, a cylindrical lens having positive refractive power only in the Z-axis direction (see FIGS. 28 to 30), or an anamorphic lens having different refractive power in the Y-axis direction and in the Z-axis direction.

Figure 31:
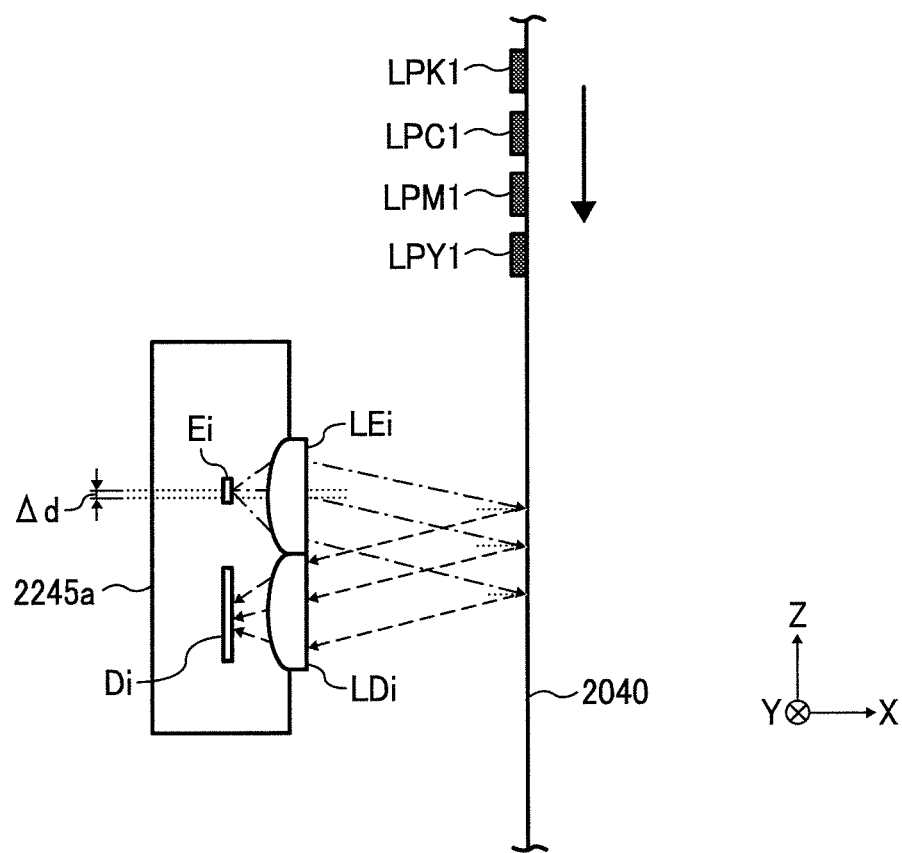
FIG. 31 is a schematic for explaining another modification example of condenser lenses (part 1)
Figure 32:
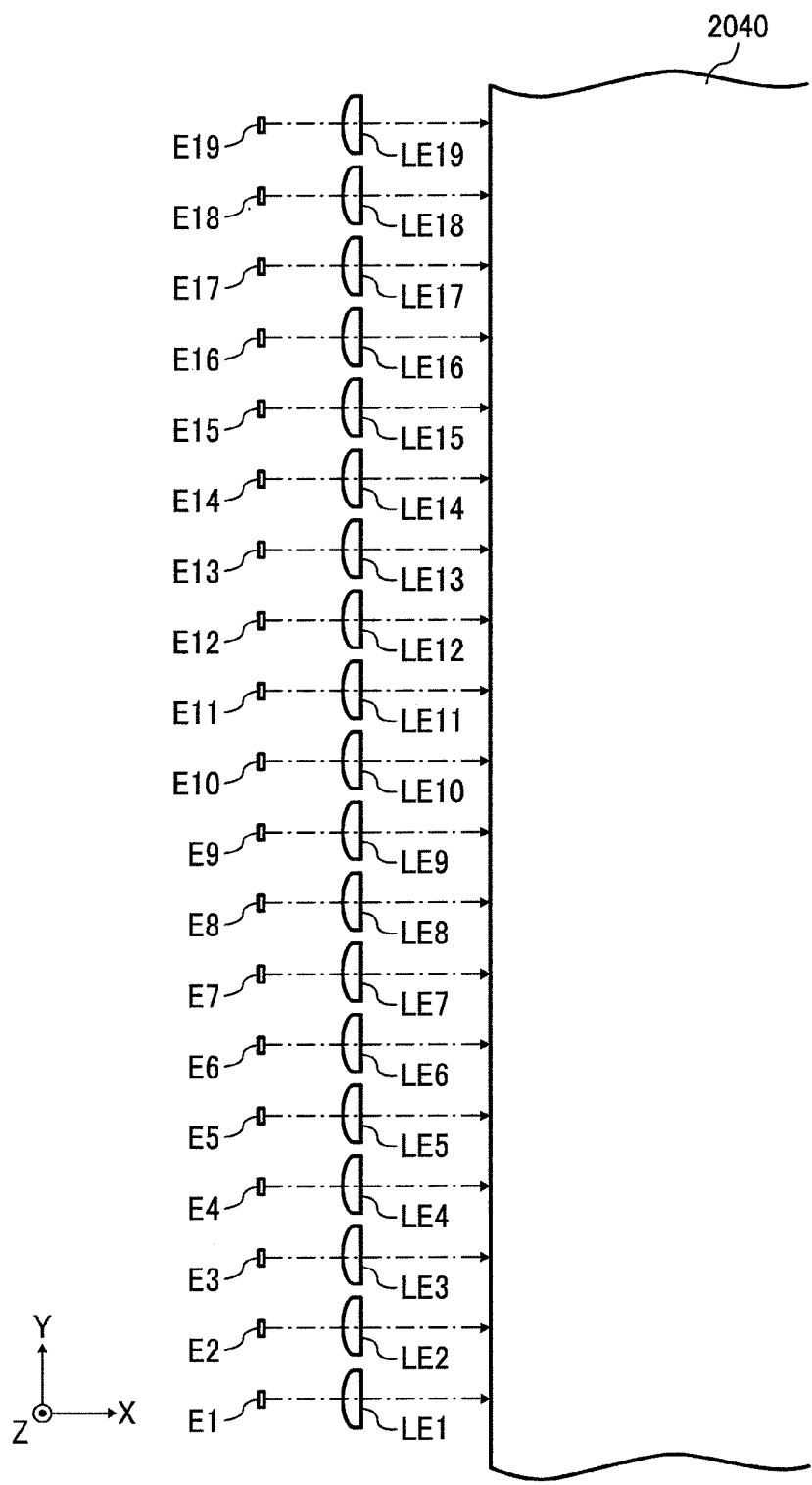
FIG. 32 is a schematic for explaining another modification example of the condenser lenses (part 2)
Figure 33:
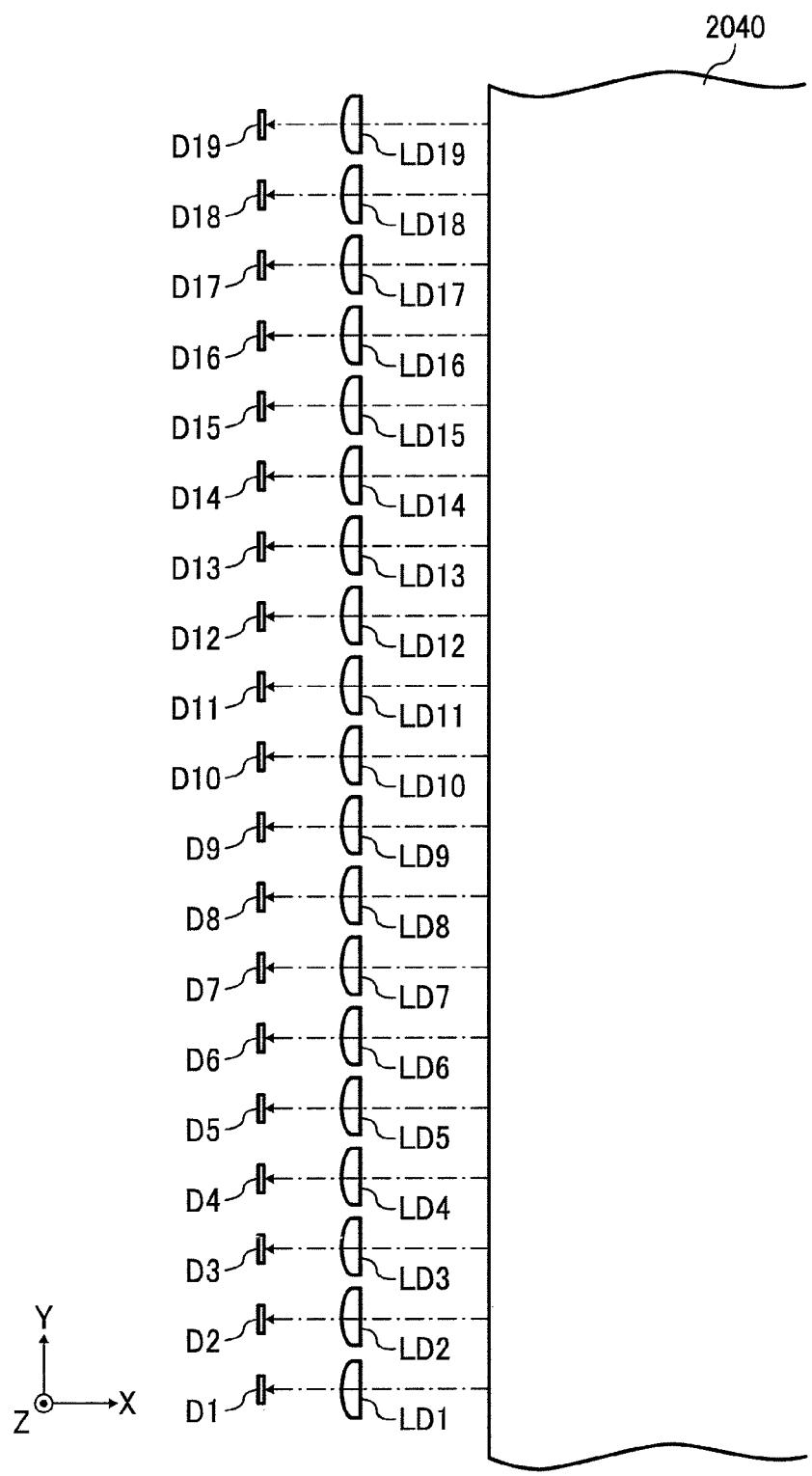
FIG. 33 is a schematic for explaining another modification example of the condenser lenses (part 3)

As illustrated in FIGS. 31 to 33 as an example, the spherical lens may be a lens having light-condensing power on the incident plane but not having the light-condensing power on the output plane.

Figure 34:
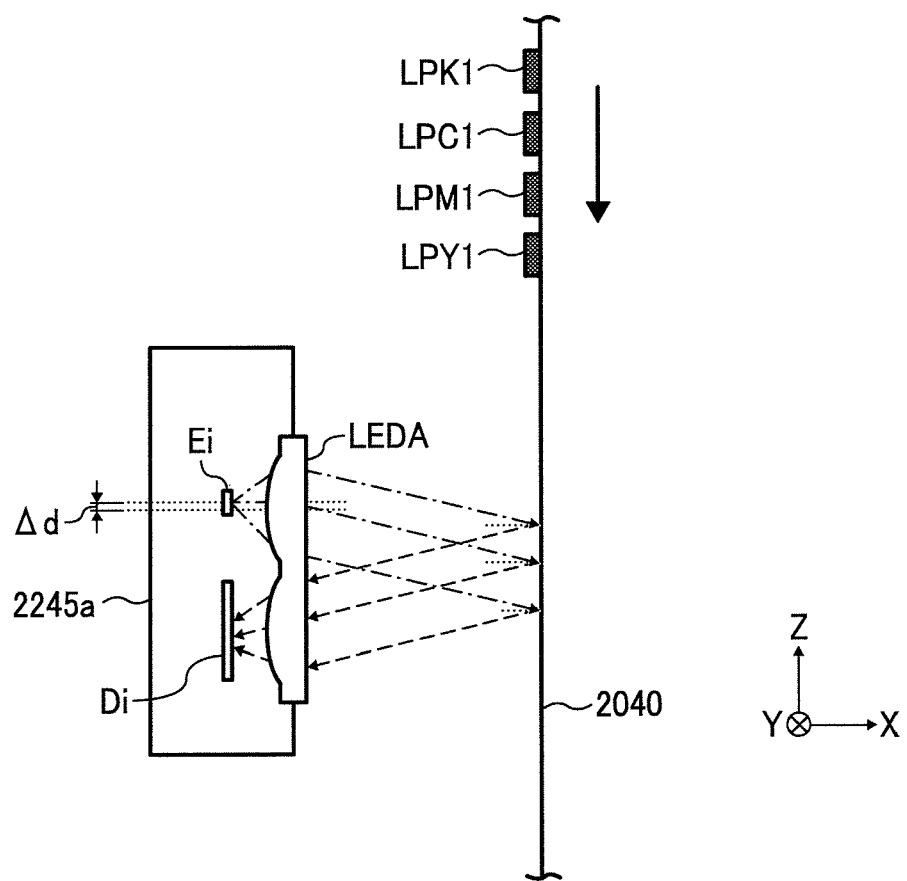
FIG. 34 is a schematic for explaining the integration of an illuminating condenser lens and a light-receiving condenser lens (part 1)
Figure 35:
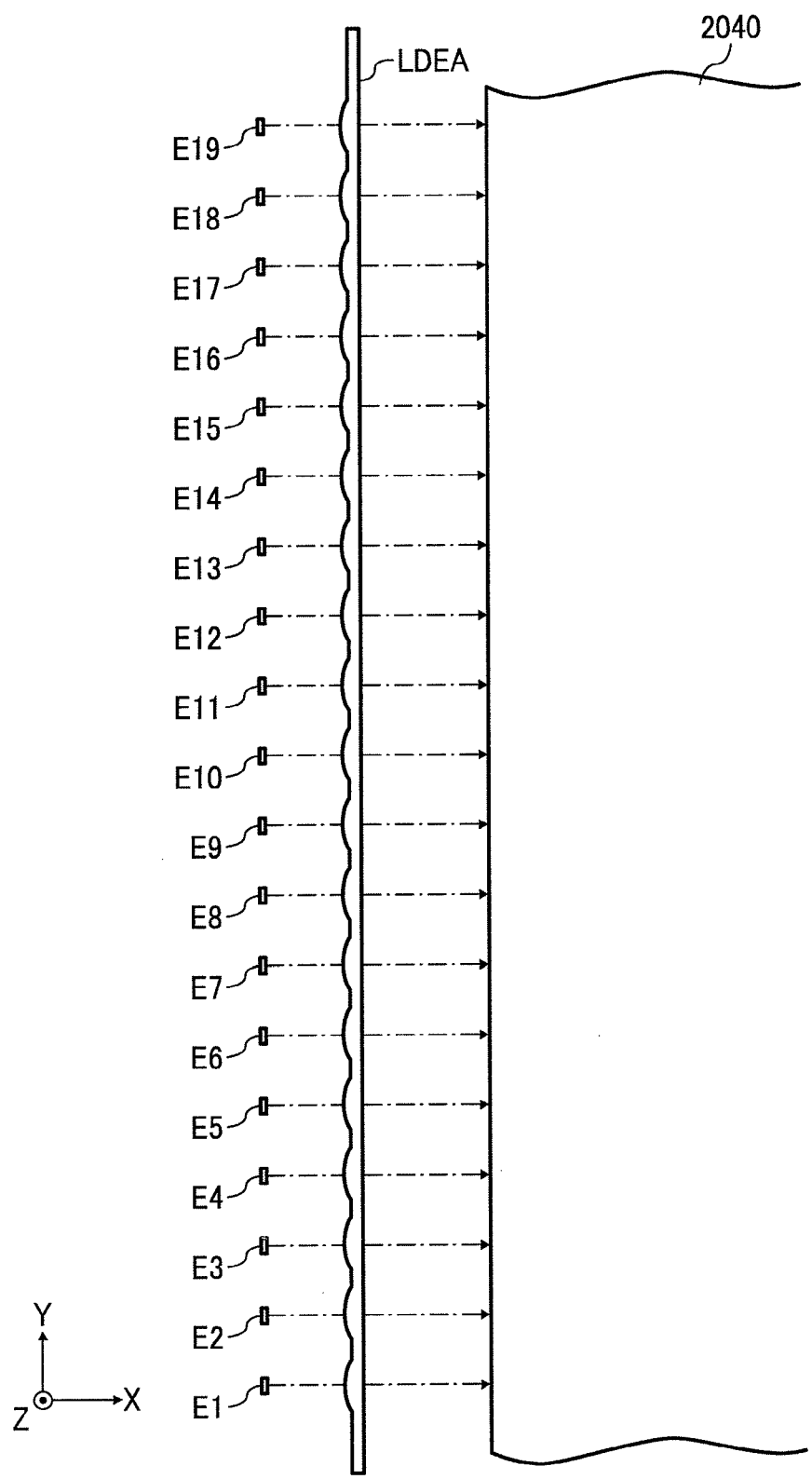
FIG. 35 is a schematic for explaining the integration of the illuminating condenser lens and the light-receiving condenser lens (part 2)
Figure 36:
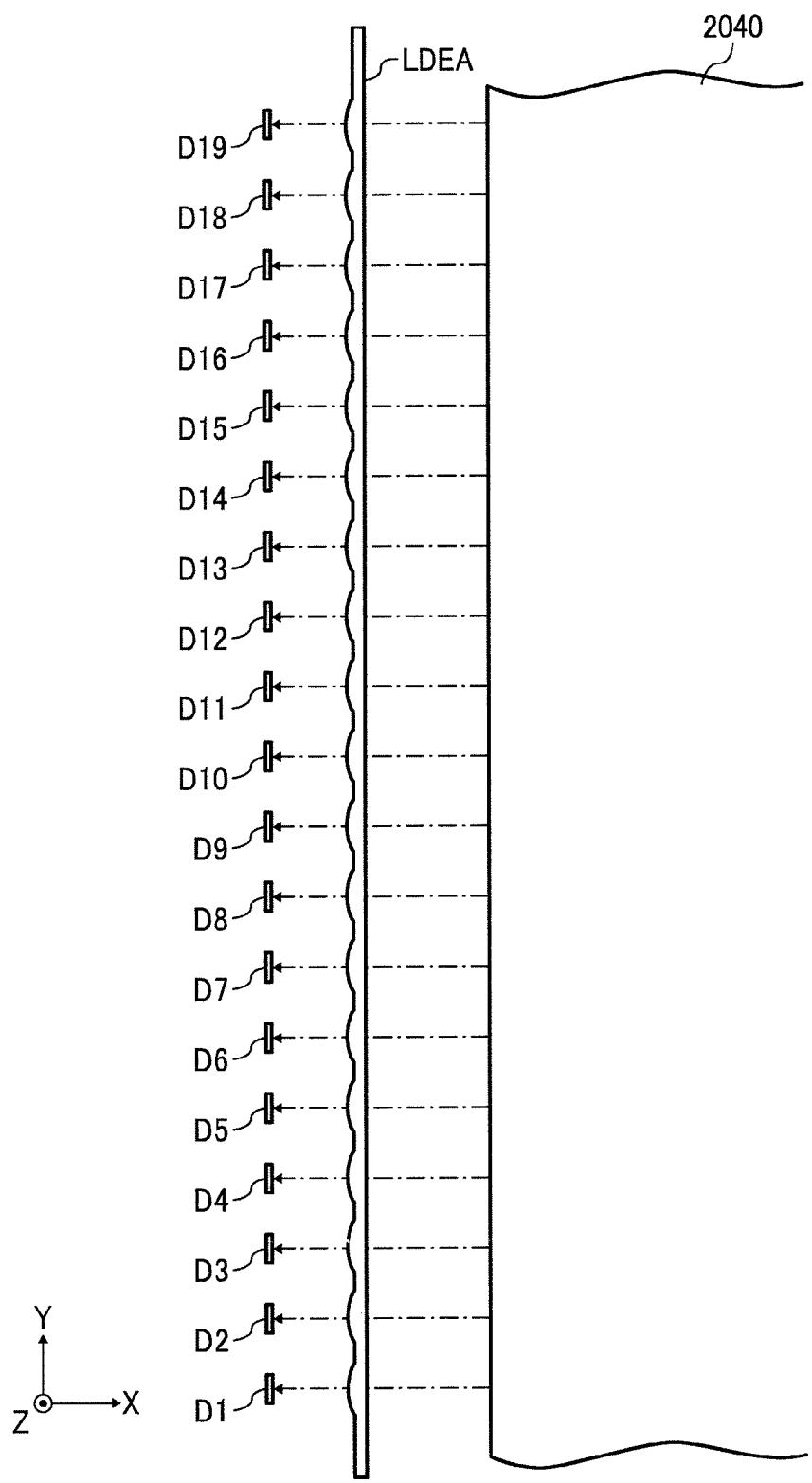
FIG. 36 is a schematic for explaining the integration of the illuminating condenser lens and the light-receiving condenser lens (part 3)
Figure 37A:
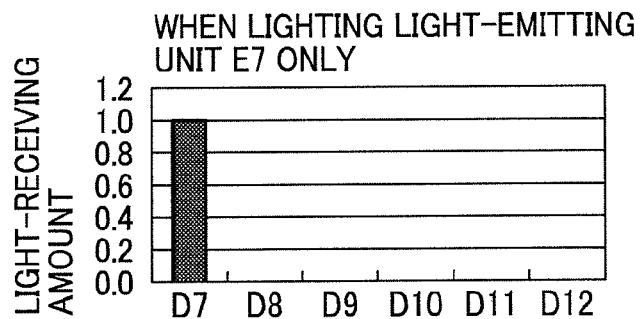
FIGS. 37A to 37F are schematics for explaining the light-receiving amount of respective light-receiving units (D7 to D12) when detecting light (S7 to S12) are reflected on a surface of the transfer belt.
Figure 37B:
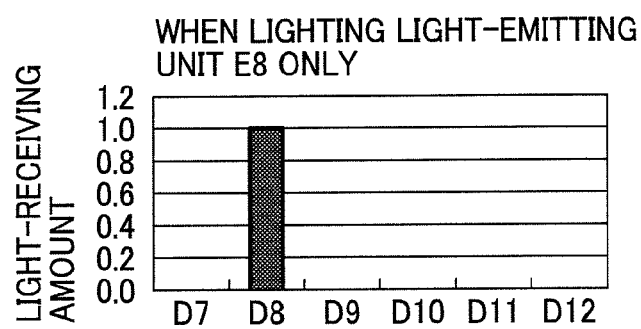
Figure 37C:
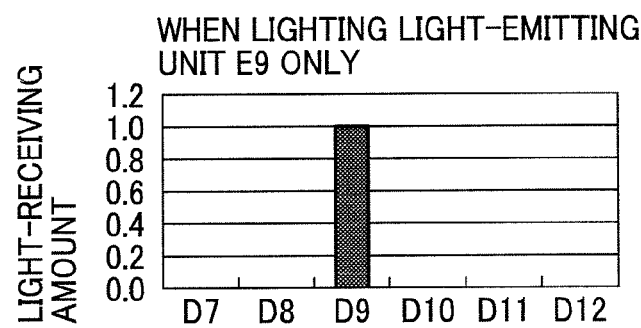
Figure 37D:
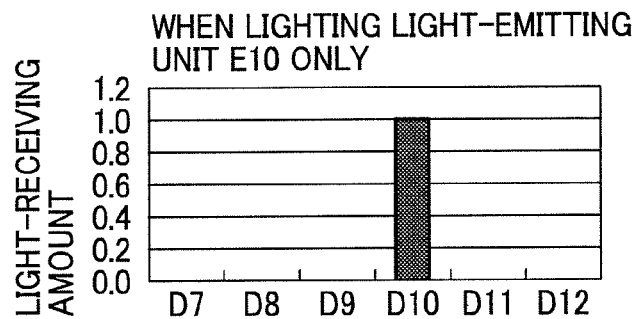
Figure 37E:
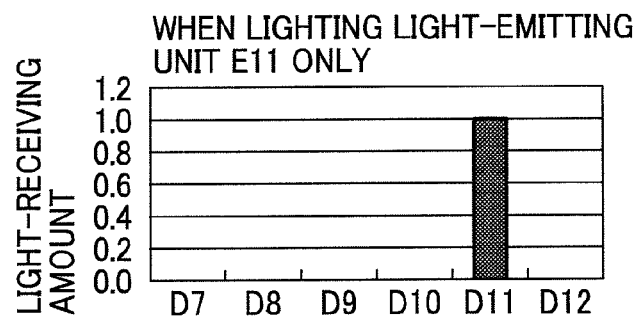
Figure 37F:
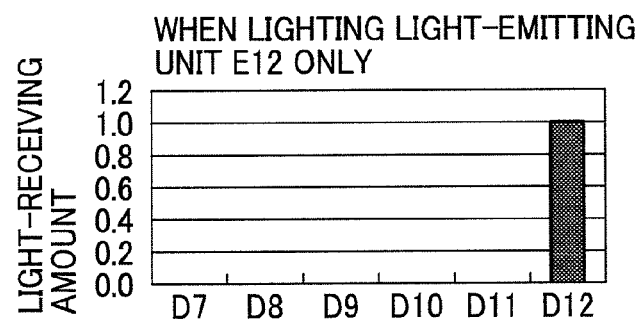
Figure 38:
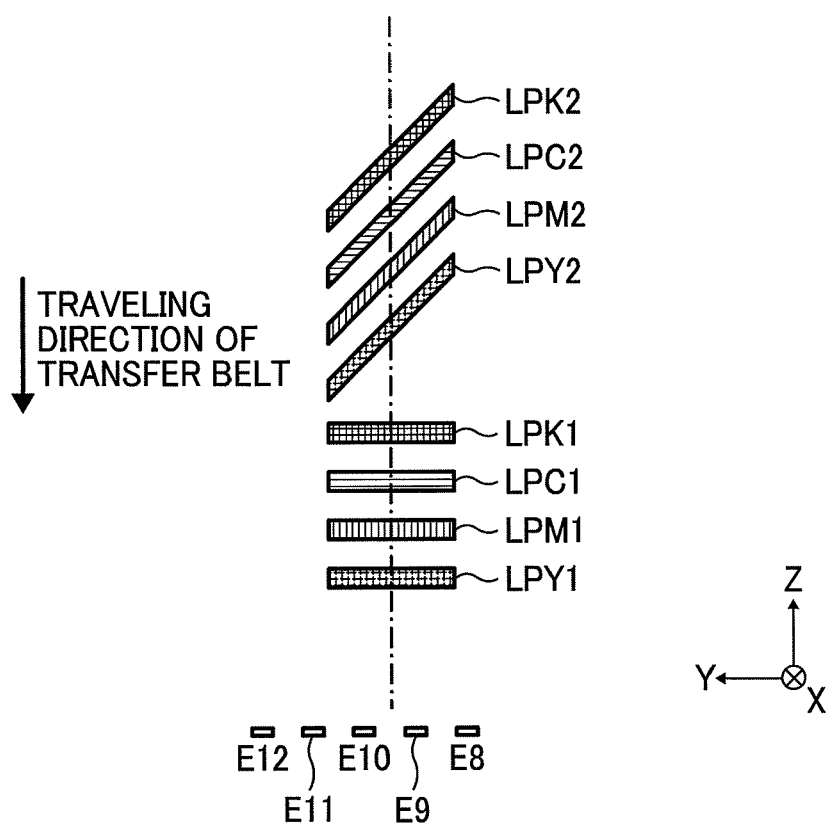
FIG. 38 is a schematic for explaining position detecting process (part 1)

Furthermore, as illustrated in FIGS. 34 to 36 as an example, the illuminating optical system and the light-receiving optical system may be integrated together as an illuminating and receiving optical system LEDA. In this case, the workability in manufacturing the reflective optical sensor is improved. The alignment accuracy between lens planes is also enhanced. The lens planes can be formed on a glass substrate or a resin substrate using a processing method such as photolithography and nanoimprint. The lens may have light-condensing power on its output plane.

The position detecting process and density detecting process using the toner pattern detector 2245 will now be explained. The reflective optical sensor illustrated in FIGS. 34 to 36 is used here. For the sake of convenience, the amount of light received by the light-receiving unit Di when the light-emitting unit Ei is lit and the detecting light Si is regularly reflected by the transfer belt 2040 is defined here as 1 (see FIGS. 37A to 37F).

Because the position detecting patterns are conveyed to the position irradiated with the detecting light from the reflective optical sensor prior to the density detecting patterns (see FIG. 7), the position detecting process is carried out prior to the density detecting process. By design, the toner patterns are formed and transferred onto the transfer belt 2040 such that the center position between the light-emitting unit E9 and the light-emitting unit E10 coincides with the center position of the toner patterns with respect to the main direction (see FIG. 38).

The printer control device 2090 lights up the light-emitting unit E10 continuously at the timing when the position detecting pattern PP comes close to the reflective optical sensor. The detecting light output from the light-emitting unit E10 is incident on the line-shape patterns LPY1 to LPK2 in sequence along with the rotation of the transfer belt 2040, i.e., with the elapse of time (see FIG. 39A).

Figure 39A:
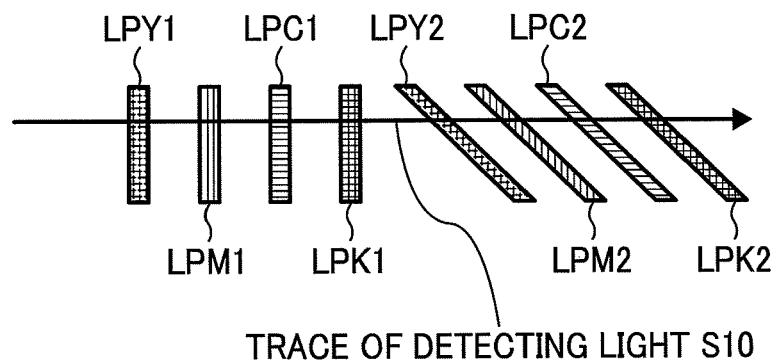
FIGS. 39A and 39B are schematics for explaining the position detecting process (part 2)
Figure 39B:
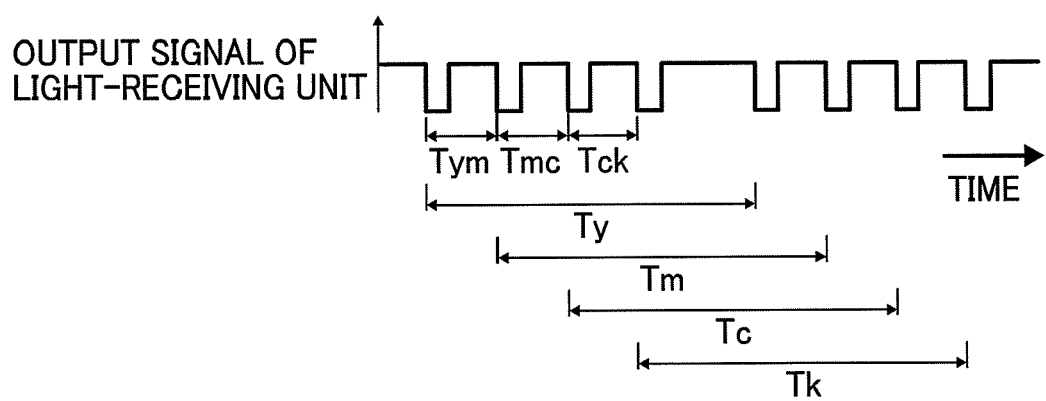

The printer control device 2090 temporally traces the output signal of each of the light-receiving units and detects time Tym that starts when the line-shape pattern LPY1 is irradiated with the detecting light and ends when the line-shape pattern LPM1 is irradiated with the detecting light, time Tmc that starts when the line-shape pattern LPM1 is irradiated with the detecting light and ends when the line-shape pattern LPC1 is irradiated with the detecting light, and time Tck that starts when the line-shape pattern LPC1 is irradiated with the detecting light and earls when the line-shape pattern LPK1 is irradiated with the detecting light (see FIG. 39B). For the sake of easier understanding, it is assumed that the output signals of the respective light-receiving units are amplified and inverted and compared with a designated reference level in a comparator circuit.

The printer control device 2090 determines that the positional relationship between the respective toner images with respect to the sub direction is appropriate when the time Tym, the time Tmc, and the time Tck are nearly the same. On the other hand, the printer control device 2090 determines that there are some misalignments in the positional relationship between the respective toner images with respect to the sub direction when the time Tym, the time Tmc, and the time Tck are not nearly the same. In this case, the printer control device 2090 obtains the amount of misalignment in the positional relationship based on the time differences of the time Tym, the time Tmc, and the time Tck, and forwards the amount of misalignment to the scanning control device. The scanning device then adjusts the timing to start scanning the light in the corresponding station such that the amount of misalignment becomes 0.

Further, the printer control device 2090 detects time Ty that starts when the line-shape pattern LPY1 is irradiated with the detecting light and ends when the line-shape pattern LPY2 is irradiated with the detecting light, time Tm that starts when the line-shape pattern LPM1 is irradiated with the detecting light and ends when the line-shape pattern LPM2 is irradiated with the detecting light, time Tc that starts when the line-shape pattern LPC1 is irradiated with the detecting light and ends when the line-shape pattern LPC2 is irradiated with the detecting light, and time Tk that starts when the line-shape pattern LPK1 is irradiated with the detecting light and ends when until the line-shape pattern LPK2 is irradiated with the detecting light (see FIG. 39B).

The printer control device 2090 then compares the time Ty, the time Tm, the time Tc, and the time Tk with their reference time obtained in advance. The printer control device 2090 determines that the positional relationship between the respective toner images with respect to the main direction is appropriate when all of the time Ty, the time Tm, the time Tc, and the time Tk are the same as their reference time.

Figure 40A:
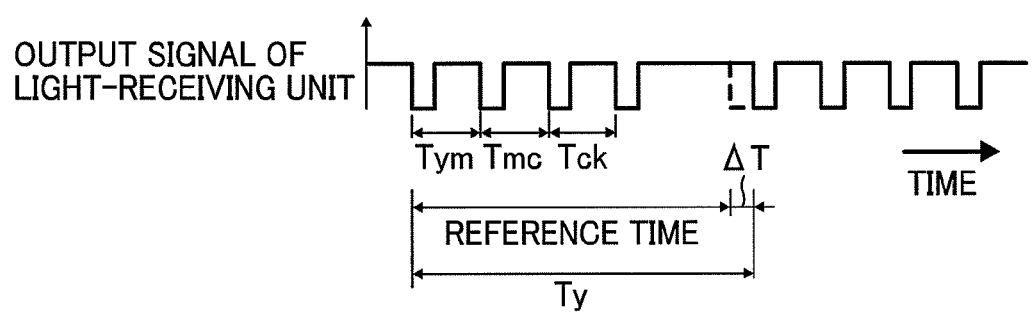
FIGS. 40A and 40B are schematics for explaining the position detecting process (part 3)
Figure 40B:
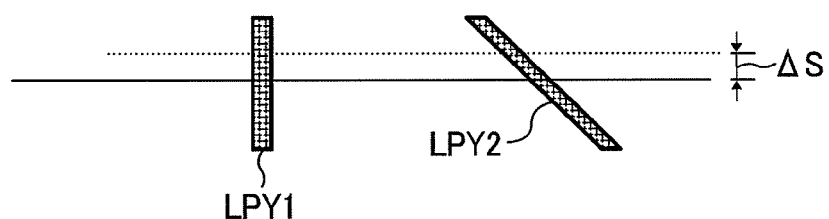

On the contrary, when the time Ty is different from its reference time, for example, the printer control device 2090 obtains the amount of misalignment $\Delta S$ of the yellow toner image with respect to the main direction using the following equation 1 (see FIGS. 40A and 40B). In the equation, V represents a travelling speed of the transfer belt 2040 in the sub direction, $\Delta T$ represents the difference between the time Ty and the reference time, and $\theta$ represents an inclined angle of the line-shape pattern LPY2 with respect to the main direction. The amount of positional misalignment $\Delta S$ is forwarded to the scanning control device.

$$\Delta S = V \cdot \Delta T \cdot \cot \theta \tag{1}$$

The scanning control device then adjusts the Y station such that the amount of positional misalignment $\Delta S$ becomes 0.

The printer control device 2090 also obtains the center position of the toner patterns with respect to the main direction from the amount of positional misalignment $\Delta S$.

As an example, the center position of the toner patterns with respect to the main direction obtained by the position detecting process above is located between the light-emitting unit E9 and the light-emitting unit E10 here. Irradiation in the rectangular patterns with two beams of detecting light is performed (S9 and S10) because the Lp of the toner pattern is 1.0 millimeter.

The position of the toner patterns is confirmed by lighting up the light-emitting units E1 to E19 in sequence based on the amount of light received by the respective light-receiving units. The fact that the amount of light received by the respective light-receiving units when the light-emitting units E9 and E10 are lit is smaller than that when other 17 pieces of the light-emitting units are lit tells that the toner patterns surely exist at the location irradiated with the detecting light S9 and S10. Accordingly, the light-emitting units E9 and E10 are used for detecting the toner density.

Figure 41:
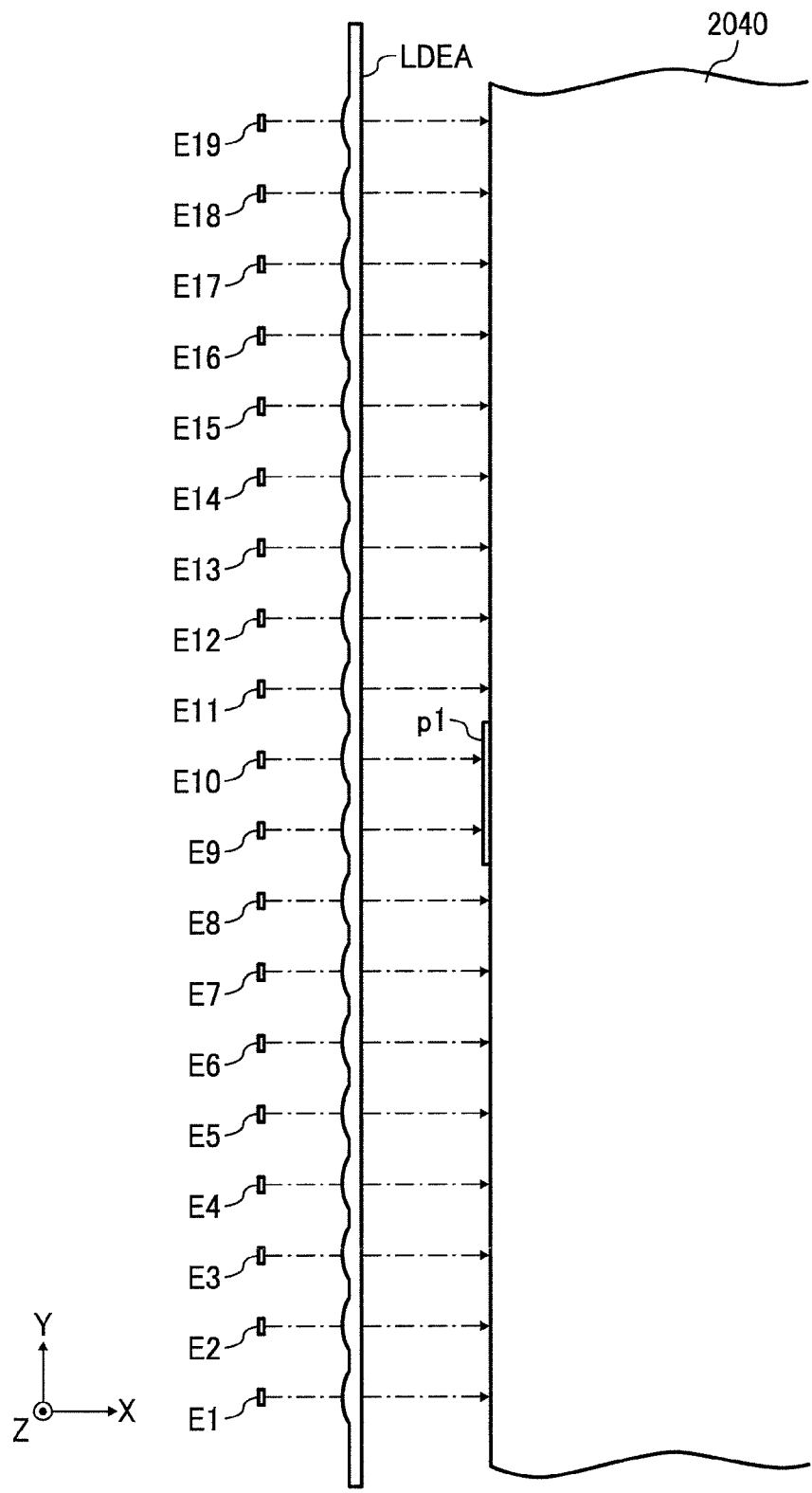
FIG. 41 is a schematic for explaining density detecting process (part 1)

As illustrated in FIG. 41 as an example, the printer control device 2090 lights up the light-emitting unit E9 and the light-emitting unit E10 sequentially and repeatedly when the rectangular patterns are conveyed in front of the reflective optical sensor.

Figure 42:
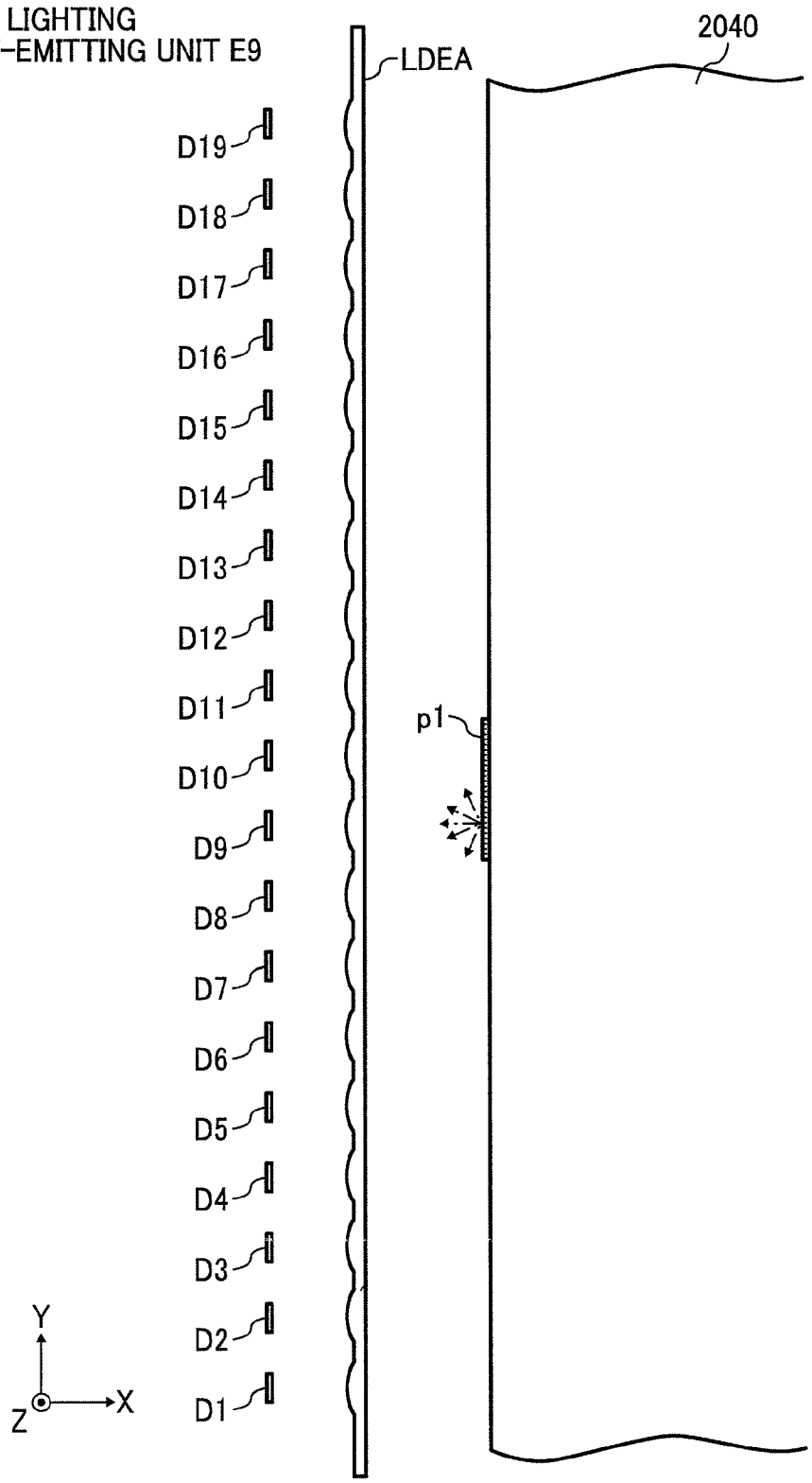
FIG. 42 is a schematic for explaining the density detecting process (part 2)
Figure 43:
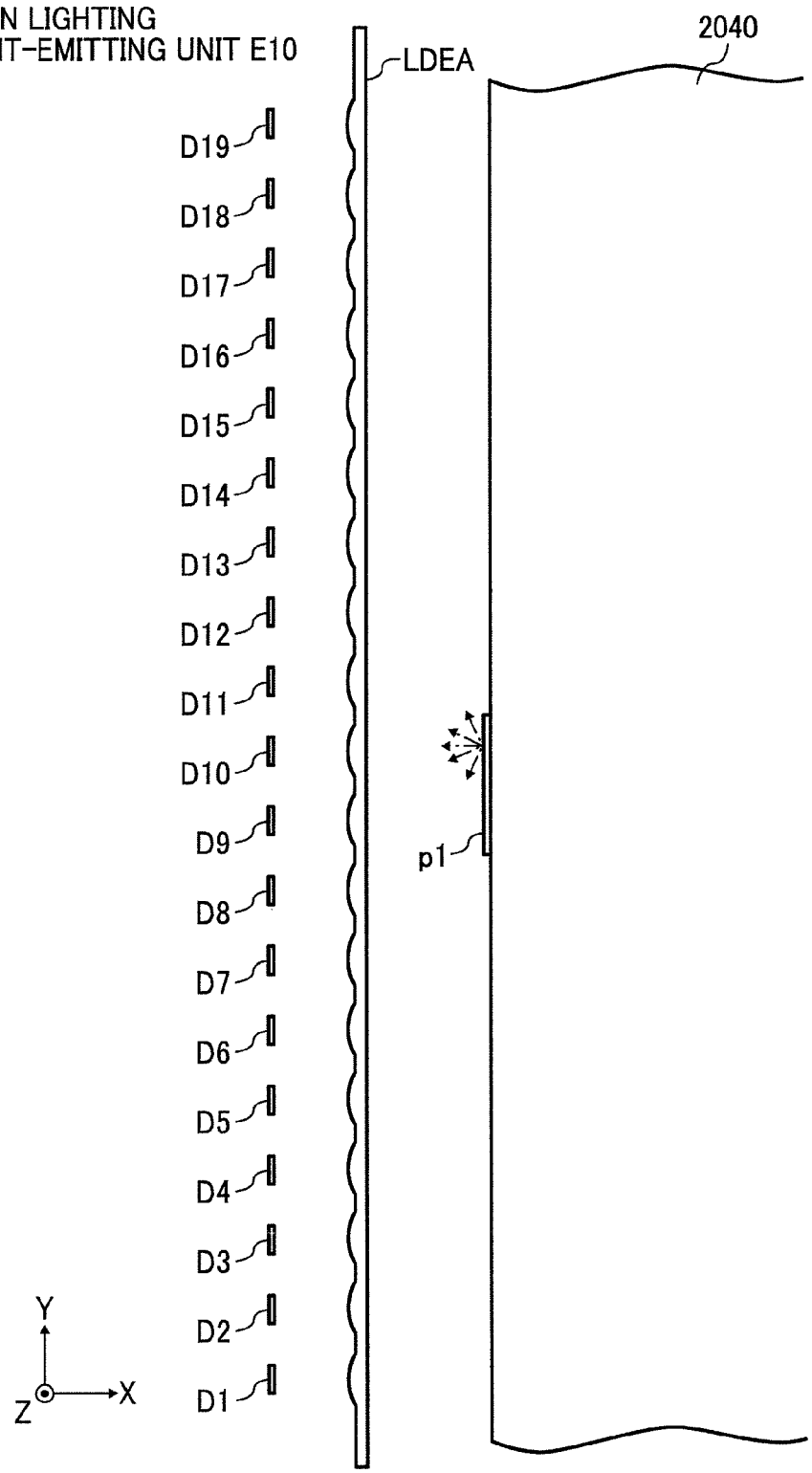
FIG. 43 is a schematic for explaining the density detecting process (part 3)

The detecting light S9 and the detecting light S10, as illustrated in FIGS. 42 and 43 as an example, reflect regularly and diffusely on the surface of the rectangular patterns. For the convenience, the light reflected regularly is also referred to as "regularly reflected light" and the light reflected diffusely is also referred to as "diffusely reflected light" here.

Processors of the respective reflective optical sensors individually obtains the amount of light received by the light-receiving units based on the output signals of the respective light-receiving units when irradiation in the rectangular patterns with the detecting light S9 is performed and stores it in a memory not shown as the detected light-receiving amount. The processors of the respective reflective optical sensor individually obtains the amount of light received by the light-receiving units based on the output signals of the respective light-receiving units when irradiation in the rectangular patterns with the detecting light S10 is performed and stores it in the memory not shown as the detected light-receiving amount.

Figure 44A:
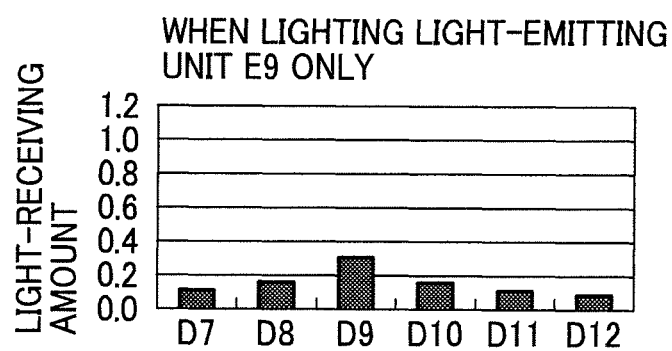
FIG. 44A is a schematic for explaining the light-receiving amount of the light-receiving units (D7 to D12) in the density detecting process when the detecting light S9 is reflected by the density detecting patterns.

FIG. 44A depicts the amount of light received by the light-receiving units when irradiation in the rectangular patterns with the detecting light S9 is performed. In this case, while the regularly reflected light received by the light-receiving unit D9 decreases compared with when the transfer belt 2040 is irradiated with the detecting light S9, the diffusely reflected light is received by the light-receiving units other than the light-receiving unit D9.

Figure 44B:
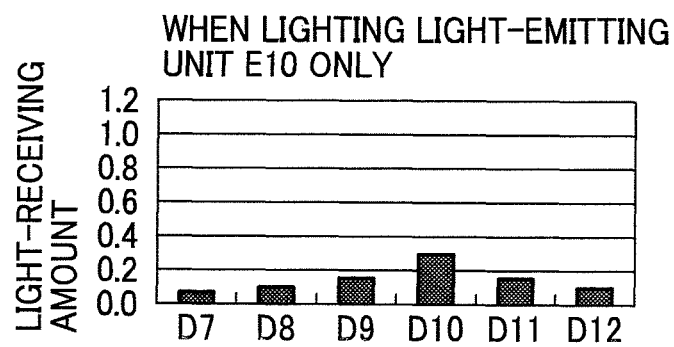
FIG. 44B is a schematic for explaining the light-receiving amount of the light-receiving units (D7 to D12) in the density detecting process when the detecting light S10 is reflected by the density detecting patterns.

FIG. 44B depicts the amount of light received by the light-receiving units when irradiation in the rectangular patterns with the detecting light S10 is performed. In this case, while the regularly reflected light component received by the light-receiving unit D10 decreases compared with when the transfer belt 2040 is irradiated with the detecting light S10, the diffusely reflected light is received by the light-receiving units other than the light-receiving unit D10.

Generally, as the toner density of rectangular pattern increases, the regularly reflected light from the rectangular pattern decreases in proportion, while the diffusely reflected light from the rectangular pattern increases proportionately.

Figure 45A:
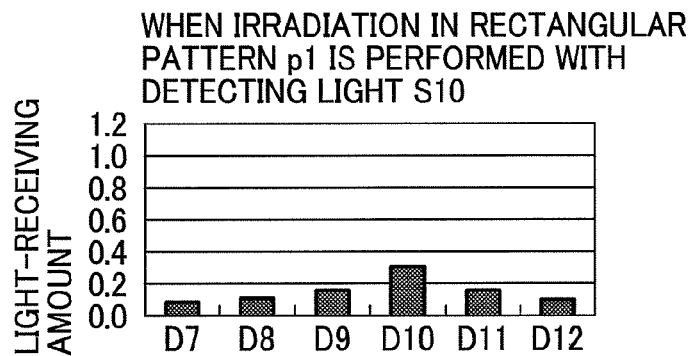
FIGS. 45A to 45E are schematics for explaining the light-receiving amounts of the respective light-receiving units (D7 to D12) in the density detecting process when the detecting light S10 is reflected by each rectangular pattern.
Figure 45B:
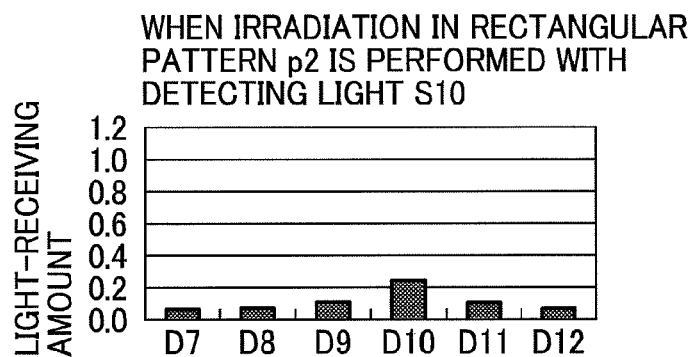
Figure 45C:
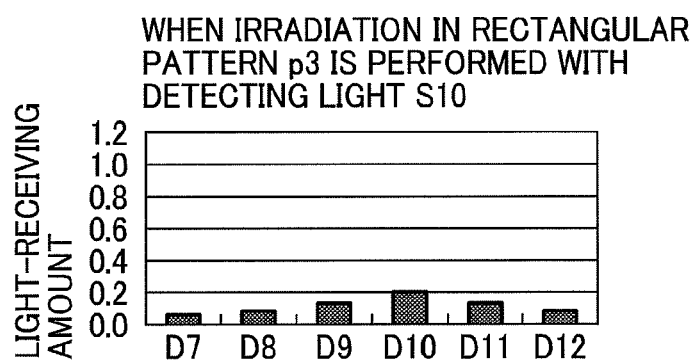
Figure 45D:
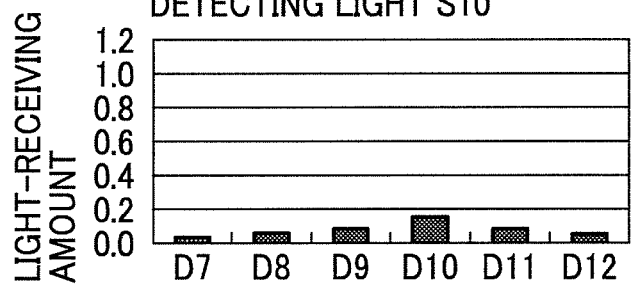
Figure 45E:
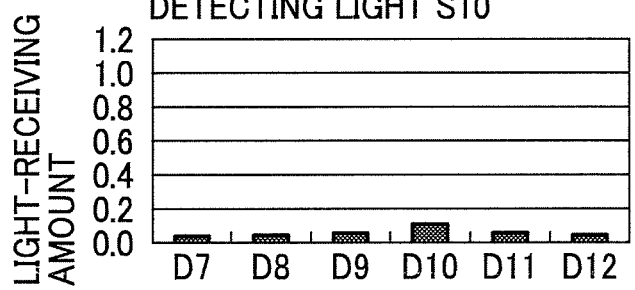

FIG. 45A illustrates, as an example, the amount of light received by the light-receiving units D7 to D12 when the rectangular pattern p1 is irradiated with the detecting light S10. FIG. 45B illustrates, as an example, the amount of light received by the light-receiving units D7 to D12 when the rectangular pattern p2 is irradiated with the detecting light S10. FIG. 45C illustrates, as an example, the amount of light received by the light-receiving units D7 to D12 when the rectangular pattern p3 is irradiated with the detecting light S10. FIG. 45D illustrates, as an example, the amount of light received by the light-receiving units D7 to D12 when the rectangular pattern p4 is irradiated with the detecting light S10. FIG. 45E illustrates, as an example, the amount of light received by the light-receiving units D7 to D12 when the rectangular pattern p5 is irradiated with the detecting light S10. As can be seen, the higher toner density is directly related to the lower amount of light received by the light-receiving units.

The printer control device 2090 determines whether the toner density in yellow is appropriate based on the detected light-receiving amount from the processor of the reflective optical sensor 2245a, whether the toner density in magenta is appropriate based on the received light amount detected from the processor of the reflective optical sensor 2245b, whether the toner density in cyan is appropriate based on the received light amount detected from the processor of the reflective optical sensor 2245c, and whether the toner density in black is appropriate based on the received light amount detected from the processor of the reflective optical sensor 2245d. When the toner density is not appropriate, the printer control device 2090 controls the developing process system of the corresponding station to make it appropriate.

As explained in the foregoing, the color printer 2000 according to the present embodiment includes four photosensitive drums (2030a, 2030b, 2030c, and 2030d), the light-scanning device scanning each of the photosensitive drums in the main direction with the light fluxes modulated in response to the image information and forming the latent images on the surfaces of the respective photosensitive drums, four developing rollers (2033a, 2033b, 2033c, and 2033d) adhering toner to the latent images to form toner images, the transfer roller 2042 transferring the toner images onto the transfer belt 2040, the toner pattern detector 2245 that detects the position of the toner pattern transferred onto the transfer belt 2040 with respect to the main direction, the position of the toner pattern with respect to the sub direction, and the toner density of the toner pattern, and the printer control device 2090 wholly controlling the printer.

The toner pattern detector 2245 has four reflective optical sensors (2245a, 2245b, 2245c, and 2245d).

The reflective optical sensors are disposed in a single row along the Y-axis direction and each has 19 pieces of the light-emitting units (E1 to E19) outputting light flux towards the transfer belt 2040, 19 pieces of the illuminating condenser lenses (LE1 to LE19) guiding the light fluxes output from the respective light-emitting units to the surface of the transfer belt 2040, 19 pieces of the light-receiving condenser lenses (LD1 to LD19) condensing and guiding the light flux reflected by the transfer belt 2040 or the toner patterns to the respective light-receiving units, 19 pieces of the light-receiving units (D1 to D19) receiving the light flux reflected by the transfer belt 2040 or the toner patterns, and the processor.

The optical axis of the illuminating condenser lens LEi is parallel to the axis passing through the center of and perpendicular to the light-emitting plane of the light-emitting unit Ei, and is off-center towards the light-receiving unit Di side. In this case, even when the toner patterns are smaller than that of a conventional one, the position of the toner patterns and the toner density of the toner patterns can be detected with a high accuracy.

The optical axis of the light-receiving condenser lens LDi is parallel to the axis passing through the center of and perpendicular to the light-receiving plane of the light-receiving unit Di, and is off-center towards the illuminating condenser lens LEi side. In this case, even when the toner patterns are smaller than that of a conventional one, the position and the toner density of the toner patterns can be detected with higher accuracy.

The printer control device 2090 then determines whether the positional relationship between the toner images with respect to the sub direction is appropriate and whether the positional relationship between the toner images with respect to the main direction is appropriate based on the output signal of the light-receiving unit when irradiation in the position detecting patterns with the detecting light is performed. When the positional relationship is not appropriate, the printer control device 2090 instructs the scanning control device to make it appropriate.

The printer control device 2090 determines whether the toner density is appropriate based on the output signals of the respective light-receiving units when irradiation in the density detecting patterns with the detecting light is performed. When the toner density is not appropriate, the printer control device 2090 controls the developing process system of the corresponding station to make it appropriate.

Consequently, the color printer 2000 can maintain the high image quality without deteriorating the workability.

In the present embodiment, the size (area) of the toner patterns can be made equal to or smaller than one hundredth of that of a conventional one. Therefore, the amount of non-contributing toner can be substantially reduced from that of the conventional one. Consequently, the replacement cycle of the toner cartridge can be extended.

In the present embodiment, the size of the toner patterns in the sub direction can be made equal to or less than one fifth of that of a conventional one. Therefore, the time required for forming the toner patterns can be shortened from that of the conventional one. For example, high detecting accuracy can be maintained with a density detecting pattern having a length of about three millimeters in the present embodiment while a density detecting pattern is required to have a length of 15 millimeters in the conventional one.

In the present embodiment in the foregoing, the position detecting patterns are conveyed to the location at which irradiation in the patterns with the detecting light is performed from the reflective optical sensor prior to the density detecting patterns. The present invention is not limited as such and the density detecting patterns may be conveyed to the location irradiated with the detecting light from the reflective optical sensor prior to the position detecting patterns. In this case, the density detecting process is carried out prior to the position detecting process.

In such a case, the printer control device 2090 can obtain the center position of the density detecting patterns with respect to the main direction using the density detecting patterns. This method will be briefly explained.

(1) The printer control device 2090 lights up the light-emitting units E1 to E19 of the respective reflective optical sensors in sequence when the position detecting process is completed.
(2) The printer control device 2090 obtains the light-receiving amount by the light-receiving unit Di based on the output signal of the light-receiving unit Di when the light-emitting unit Ei is lit up.
(3) The printer control device 2090 finds the light-receiving unit with the light-receiving amount smaller than 1. In the present embodiment, the light-receiving amount of the light-receiving unit D9 when the light-emitting unit E9 is lit, and the light-receiving amount of the light-receiving unit D10 while the light-emitting unit E10 is lit are smaller than 1.
(4) The printer control device 2090 compares the light-receiving amount of the light-receiving unit D9 and the light-receiving amount of the light-receiving unit D10. For example, if the light-receiving amount of the light-receiving unit D9 while the light-emitting unit E9 is lit is smaller than the light-receiving amount of the light-receiving unit D10 while the light-emitting unit E10 is lit, it is determined that the center of the rectangular patterns is "shifted on the light-emitting unit E9 side" with respect to the main direction.

In this case, although it is less accurate than the position detection using the position detecting patterns, the position of the density detecting patterns with respect to the main direction can be detected with an accuracy of "arrangement pitch of the light-emitting units".

Additionally, preliminary detecting patterns for recognizing the position of density detecting patterns prior to the density detection may be added to the density detecting patterns.

In the present embodiment, it has been explained that the reflective optical sensor detects both the position and the density of toner patterns. The present invention is not limited as such and the reflective optical sensor may only detect one of the position of toner patterns or the density of toner patterns.

Figure 46:
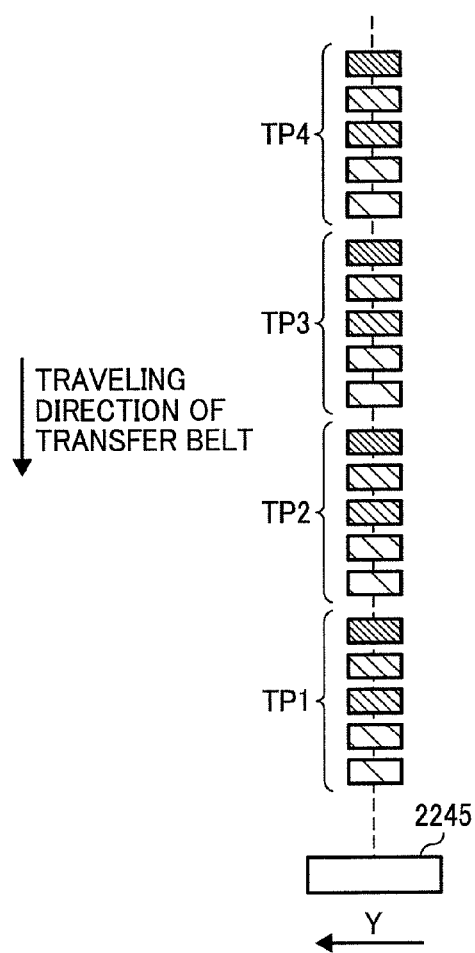
FIG. 46 is a schematic for explaining a modification example of toner patterns.

In the present embodiment, as illustrated in FIG. 46 as an example, the toner patterns TP1 to TP4 may be arranged in a single row along the traveling direction of the transfer belt 2040. In this case, the toner densities of four colors can be detected by a single reflective optical sensor.

In the present embodiment, the printer control device 2090 may carry out at least a part of the process performed by the processors of the respective reflective optical sensors.

In the present embodiment, it has been explained that the center position of the density detecting patterns with respect to the main direction is located between the light-emitting unit E9 and the light-emitting unit E10. The location is not limited as such.

In the present embodiment, it has been explained that each of the reflective optical sensors has 19 pieces of light-emitting units. However, the number of light-emitting units is not limited as such. In short, the reflective optical sensor only needs to have three or more light-emitting units.

In the present embodiment, it has been explained that 19 pieces of the light-emitting units (E1 to E19) are arranged in a row along the Y-axis direction. However, the arrangement is not limited to that. The light-emitting units may be arranged along a direction inclined with respect to the Y-axis direction, or arranged in multiple rows along the Y-axis direction in a so-called zigzag alignment. In short, the light-emitting units only need to be arranged at equal intervals with respect to the Y-axis direction.

In the present embodiment, it has been explained that the number of light-emitting units and the number of light-receiving units are the same. However, the present invention is not limited as such.

In the present embodiment, each of the reflective optical sensors may not have the receiving optical system, as illustrated in FIG. 19 as an example if the detecting sensitivity is not adversely affected.

In the present embodiment, each of the reflective optical sensors may not have the illuminating optical system, as illustrated in FIG. 26 as an example if the detecting sensitivity is not adversely affected.

In the present embodiment, the color printer 2000 including multiple photosensitive drums has been explained as an image forming apparatus. However, the image forming apparatus is not limited to that and the present invention can be applied to, for example, a printer including a single photosensitive drum that forms an image of a single color.

In the present embodiment, the toner patterns on the transfer belt 2040 are detected. However, subject of the detection is not limited as such. In other embodiments of image forming apparatuses, the toner patterns on a photoconductor or an intermediate transfer belt may be detected.

The present invention may be applied to an image forming apparatus other than the printer, such as a copier, a facsimile, or a multifunction apparatus combining the functions thereof.

The reflective optical sensor according to the present embodiment can be used to detect the toner density and the position of the toner image on the photosensitive drum.

Figure 47:
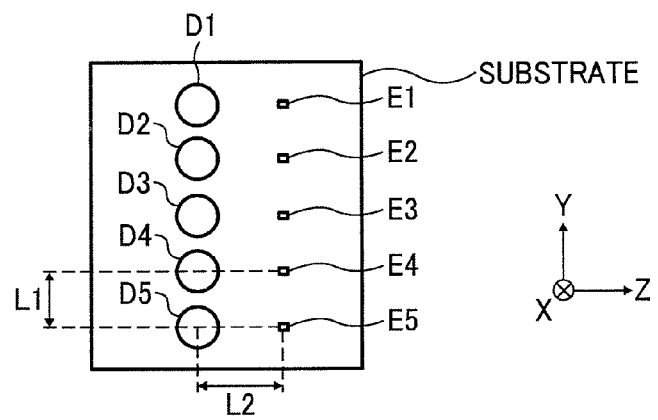
FIG. 47 is a schematic for explaining a modification example of a reflective optical sensor with integrated light-emitting units and light-receiving units (part 1)
Figure 48:
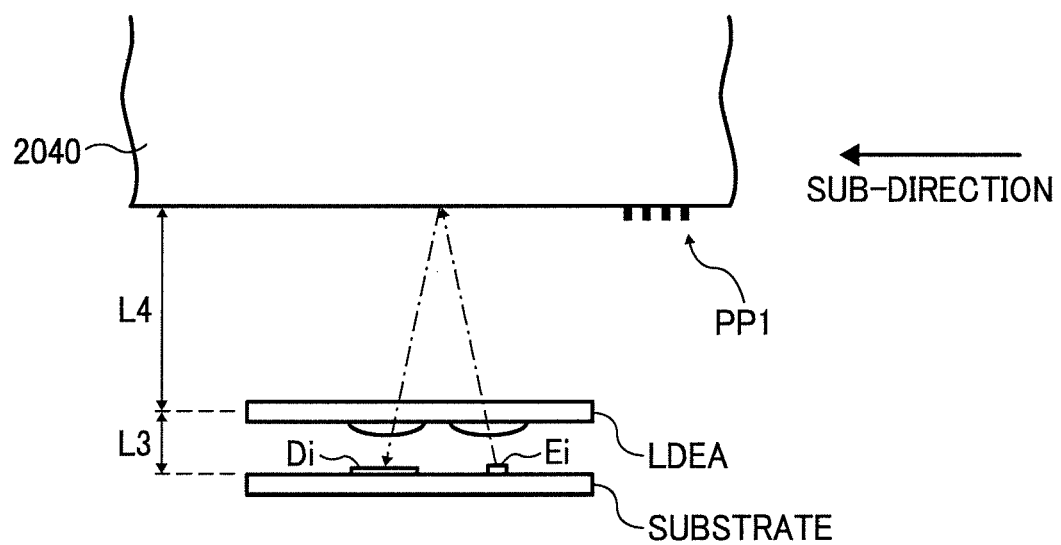
FIG. 48 is a schematic for explaining the modification example of the reflective optical sensor with integrated light-emitting units and light-receiving units (part 2).

In the present embodiment, as illustrated in FIG. 47 as an example, a plurality of light-emitting units and a plurality of light-receiving units may be formed on the same substrate (semiconductor substrate) using a semiconductor manufacturing process. In this case, each of the light-emitting units (E1 to E5) may be in a square form of 40 micrometers by 40 micrometers and each of the light-receiving units (D1 to D5) may be in a round shape of 300 micrometers in diameter. It is desirable that the symbol L1 shown in FIG. 47 be about 400 micrometers and the symbol L2 be about 500 micrometers. With such an arrangement, as illustrated in FIG. 48 as an example, the distance (L3+L4) between the substrate and the transfer belt 2040 can be set to about 6 millimeters, allowing the transfer belt 2040 to be irradiated with the detecting light at an incident angle of 2.6 degrees. As an example, the symbol L3 shown in FIG. 48 can be set to 1.05 millimeters and the symbol L4 can be set to 5 millimeters.

In this reflective optical sensor, the multiple light-emitting units lie bare, and the light output from the multiple light-emitting units are output from the illuminating system without passing through any other members.

With such a structure, even when the distance between the substrate and the transfer belt 2040 is changed by the flapping and such of the transfer belt 2040, the light path of the detecting light reflected by the transfer belt 2040 or by the toner patterns can be prevented from being displaced from the light path heading for the light-receiving unit, thereby stably maintaining a high detection accuracy. With a conventional reflective optical sensor, the incident angle of the detecting light is about 10 degrees, and the changes in the distance between the substrate and the transfer belt 2040 causes the fluctuation in the detecting accuracy.

According to an embodiment of the present invention, even when the toner pattern is small, at least one of the position of the toner pattern or the toner density of the toner pattern is detected with a high accuracy.

Further, according to an embodiment of the present invention, high image quality is maintained without deteriorating the workability.

(Note 1) According to one aspect of the present invention, an image forming apparatus may include:
an image carrier;
a light-scanning device that scans the image carrier in a main-scanning direction with light flux modulated in response to image information to form a latent image on the image carrier;
a developing device that adheres toner to the latent image to create a toner image;
a transfer device that transfers the toner image to a medium; and
the reflective optical sensor according to claim 11 that detects at least one of a position and a toner density of the toner pattern on the image carrier or the medium.

(Note 2) In the above aspect of the present invention, in the image forming apparatus, the image information may be image information in multiple colors.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A reflective optical sensor detecting at least one of a position of a toner pattern and a toner density of the toner pattern, the reflective optical sensor comprising:
an illuminating system that has at least three light-emitting units;
a light-receiving system that has at least three light-receiving units and receives light output from the illuminating system and reflected by the toner pattern; and
an illuminating optical system that includes at least three illuminating condenser lenses individually corresponding to the at least three light-emitting units and that guides the light output from the illuminating system to the toner pattern, wherein
the at least three light-emitting units and the at least three light-receiving units are both arranged in equal distance with respect to one direction, and
optical axes of the at least three illuminating condenser lenses are off-center in parallel to an axis passing through a center of and perpendicular to the corresponding light-emitting unit.

2. The reflective optical sensor according to claim 1, wherein the optical axes of the at least three illuminating condenser lenses are off-center on the light-receiving system side with respect to the axis passing through the center of and perpendicular to the corresponding light-emitting unit.

3. The reflective optical sensor according to claim 1, further comprising a light-receiving optical system including at least three light-receiving condenser lenses individually corresponding to the at least three light-receiving units, the light-receiving optical system condensing and guiding light flux reflected by the toner pattern to the light-receiving system.

4. The reflective optical sensor according to claim 3, wherein optical axes of the at least three light-receiving condenser lenses are off-center in parallel with respect to an axis passing through a center of and perpendicular to the corresponding light-receiving unit.

5. The reflective optical sensor according to claim 4, wherein the optical axes of the at least three light-receiving condenser lenses are off-center on the illuminating optical system side with respect to the axis passing through the center of and perpendicular to the corresponding light-emitting unit.

6. The reflective optical sensor according to claim 1, wherein the at least three light-emitting units and the at least three light-receiving units are integrally formed on a same substrate.

7. The reflective optical sensor according to claim 6, wherein light output from the at least three light-emitting units are output from the illuminating system without passing through any other members.

8. The reflective optical sensor according to claim 6, wherein the toner pattern is irradiated with light flux output from the illuminating system at an incident angle equal to or less than five degrees.

9. An image forming apparatus comprising:
an image carrier;
a light-scanning device that scans the image carrier in a main-scanning direction with light flux modulated in response to image information to form a latent image on the image carrier;
a developing device that adheres toner to the latent image to create a toner image;
a transfer device that transfers the toner image to a medium; and
the reflective optical sensor according to claim 1 that detects at least one of a position and a toner density of the toner pattern on the image carrier or the medium.

10. The image forming apparatus according to claim 9, wherein the image information is image information in multiple colors.

11. A reflective optical sensor detecting at least one of a position of a toner pattern and a toner density of the toner pattern, the reflective optical sensor comprising:
an illuminating system that has at least three light-emitting units;
a light-receiving system that has at least three light-receiving units and receives light output from the illuminating system and reflected by the toner pattern; and a light-receiving optical system that includes at least three light-receiving condenser lenses individually corresponding to the at least three light-emitting units and that condenses and guides light reflected by the toner pattern to the light-receiving system, wherein the at least three light-emitting units and the at least three light-receiving units are both arranged in equal distance with respect to one direction, and optical axes of the at least three light-receiving condenser lenses are off-center in parallel to an axis passing through a center of and perpendicular to the corresponding light-receiving unit.

12. The reflective optical sensor according to claim 11, wherein the optical axes of the at least three light-receiving condenser lenses are off-center on the illuminating system side with respect to an axis passing through a center of and perpendicular to the corresponding light-emitting unit.

13. The reflective optical sensor according to claim 11, wherein the at least three light-emitting units and the at least three light-receiving units are integrally formed on a same substrate.

14. The reflective optical sensor according to claim 13, wherein light output from the at least three light-emitting units are output from the illuminating system without passing through any other members.

15. The reflective optical sensor according to claim 13, wherein the toner pattern is irradiated with light flux output from the illuminating system at an incident angle equal to or less than five degrees.

* * * * *